(12) United States Patent
VanNieuwenhze et al.

(10) Patent No.: US 10,544,444 B2
(45) Date of Patent: Jan. 28, 2020

(54) COMPOSITIONS FOR IN SITU LABELING OF BACTERIAL CELL WALLS WITH FLUOROPHORES AND METHODS OF USE THEREOF

(71) Applicant: Indiana University Research and Technology Corporation, Indianapolis, IN (US)

(72) Inventors: Michael S. VanNieuwenhze, Bloomington, IN (US); Edward Hall, Bloomington, IN (US); Erkin Kuru, Bloomington, IN (US); Pamela Brown, Columbia, MO (US); Srinivas Tekkam, Bloomington, IN (US); Velocity Hughes, Bloomington, IN (US); Yves Brun, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 16/048,000

(22) Filed: Jul. 27, 2018

(65) Prior Publication Data

US 2019/0024135 A1    Jan. 24, 2019

Related U.S. Application Data

(63) Continuation of application No. 14/395,815, filed as application No. PCT/US2013/037504 on Apr. 21, 2013, now abandoned.

(60) Provisional application No. 61/718,048, filed on Oct. 24, 2012, provisional application No. 61/636,640, filed on Apr. 21, 2012.

(51) Int. Cl.
| | |
|---|---|
| *C12Q 1/04* | (2006.01) |
| *C12Q 1/18* | (2006.01) |
| *C07C 271/20* | (2006.01) |
| *C07D 311/74* | (2006.01) |
| *C07K 9/00* | (2006.01) |
| *C12Q 1/02* | (2006.01) |

(52) U.S. Cl.
CPC ............ *C12Q 1/045* (2013.01); *C07C 271/20* (2013.01); *C07D 311/74* (2013.01); *C07K 9/003* (2013.01); *C12Q 1/025* (2013.01); *C12Q 1/18* (2013.01)

(58) Field of Classification Search
None
See application file for complete search history.

(56) References Cited

FOREIGN PATENT DOCUMENTS

WO    2012006603 A2    1/2012

OTHER PUBLICATIONS

Cava et al. (The EMBO Journal (2011) 30, 3442-3453) (Year: 2011).*
Schouten et al. (Mol. BioSyst., 2006, 2, 484-491) (Year: 2006).*
Aaron et al., "The tubulin homologue FtsZ contributes to cell elongation by guiding cell wall precursor synthesis in Caulobacter crescentus," (2007) Mol. Microbiol. 64(4):938-952.
Alberts et al., "Small molecules, energy, and biosynthesis," (1994) Molecular Biology of the Cell, Garland Publishing Inc. 3rd ed., 56-57.
Atrih et al., "Analysis of Peptidoglycan Structure from Vegetative Cells of Bacillus subtilis 168 and Role of PBP 5 in Peptidoglycan Maturation," (1999) J. Bacteriol. 181(13):3956-3966.
Baskin et al., "Copper-free click chemistry for dynamic in vivo imaging," (2007) Proc. Natl. Acad. Sci. USA 104(43):16793-16797.
Braun et al., "Synthesis of the fluorescent amino acid rac-(7-hydroxycoumarin-4-yl)ethylglycine," (2010) Beilstein J. Org. Chem. 6(69):1-4.
Brown et al., "Polar growth in the Alphaproteobacterial order Rhizobiales," (2012) Proc. Natl. Acad. Sci. USA 109:1697-1701.
Cava et al., "Emerging knowledge of regulator roles of D-amino acids in bacteria," (2011) Cell. Mol. Life Sci. 68:817-831.
Cava et al., "Distinct pathways for modification of the bacterial cell wall by non-canonical D-amino acids," (2011) EMBO J. 30:3442-3452.
Chowdhury et al., "Identification of Crosslinked Peptides after Click-based Enrichment Using Sequential CID and ETD Tandem Mass Spectrometry," (2009) Anal. Chem. 81(13):5524-5532.
Chu et al., "Isotope-Coded and Affinity-Tagged Cross-Linking (ICATXL): An Efficient Strategy to Probe Protein Interaction Surfaces," (2006) J. Am. Chem. Soc. 128:10362-10636.
Collins et al., "Isotopically Labeled Crosslinking Reagents: Resolution of Mass Degeneracy in the Identification of Crosslinked Peptides," (2003) Bioorg. Med. Chem. Lett. 13:4023-4026.
Daniel et al., "Control of Cell Morphogenesis in Bacteria: Two Distinct Ways to Make a Rod-Shaped Cell," (2003) Cell 113:767-776.
de Pedro et al., "Murein Segregation in *Escherichia coli*," (1997) J. Bacteriol. 179(9):2823-2834.
Decad et al., "Outer Membrane of Gram-Negative Bacteria XII. Molecular-Sieving Function of Cell Wall," (1976) J. Bacteriol. 128(1):325-336.
Dominguez-Escobar et al., "Processive Movement of MreB-Associated Cell Wall Biosynthetic Complexes in Bacteria," (2011) Science 333:225-228.
Evans, "The Rise of Azide-Alkyne 1,3-Dipolar 'Click' Cycloaddition and its Application to Polymer Science and Surface Modification," (2007) Aust. J. Chem., 60:384-395.
Filipe et al., "Functional Analysis of *Streptococcus pneumoniae* MurM Reveals the Region Responsible for Its Specificity in the Synthesis of Branched Cell Wall Peptides," (2011) J. Biol. Chem. 276(43):39618-39628.

(Continued)

*Primary Examiner* — Sergio Coffa
(74) *Attorney, Agent, or Firm* — Faegre Baker Daniels LLP

(57) ABSTRACT

Disclosed herein are compositions for assessing peptidoglycan biosynthesis in bacteria, for identifying bacteria, and for screening for bacterial cell wall-acting and/or cell wall-disrupting agents via modified D-amino acids and methods of use thereof. Also disclosed are live bacteria having one or more modified D-amino acids as described herein incorporated into peptidoglycan of a bacterial cell wall.

6 Claims, 20 Drawing Sheets

(56) References Cited

OTHER PUBLICATIONS

Filonov et al., "Bright and stable near infra-red fluorescent protein for in vivo imaging," (2011) Nat. Biotechnol. 29(8):757-761.
Flardh, "Growth polarity and cell division in Streptomyces," (2003) Curr. Opin. Microbiol. 6:567-571.
Furchtgott et al., "Mechanisms for maintaining cell shape in rod-shaped Gram-negative bacteria," (2011) Mol. Microbiol. 81(2):340-353.
Garner et al., "Coupled, Circumferential Motions of the Cell Wall Synthesis Machinery and MreB Filaments in B. subtilis," (2011) Science 333(6039):222-225.
International Search Report and Written Opinion dated Jun. 13, 2013, ten pages.
Jewett et al., "Cu-free click cycloaddition reactions in chemical biology," (2010) Chem. Soc. Rev. 39:1272-1279.
Kang et al., "Synthesis of Biotin Tagged Chemical Cross-linkers and Their Applications for Mass Spectrometry," (2009) Rapid Commun. Mass Spectrom. 23(11):1719-1726.
Katritzky et al., "Fluorescent amino acids: adances in protein-extrinsic flurophores," (2009) Org. Biomol. Chem. 7:627-634.
Kele et al., "Clickable fluorophores for biological labeling-with or without copper," (2009) Org. Biomol. Chem. 7:3486-3490.
Kolb et al., "Click Chemistry: Diverse Chemical Function from a Few Good Reactions," (2001) Angew. Chem. Int. Ed. 40:2004-2021.
Kuru et al., "In situ Probing of Newly Synthesized Peptidoglycan in Live Bacteria with Fluorescent D-Amino Acids," (2012) Angew. Chem. Int. Ed. Engl., 51(50):12519-12523.
Lam et al., "D-amino Acids Govern Stationary Phase Cell Wall Re-Modeling in Bacteria," (2009) Science 325(5947):1552-1555.
Lavis et al., "Bright Ideas for Chemical Biology," (2008) ACS Chem. Biol. 3(3):142-155.
Lin, "Beyond the rainbow: new fluroescent proteins brighten the infrared scene," (2011) Nature Methods 8(9):726-728.
Litzinger et al., "Muropeptide Rescue in Bacillus subtilis Involves Sequential Hydrolysis by β-N-Acetylglucosaminidase and N-Acetylmuramyl-L-Alanine Amidase," (2010) J. Bacteriol. 192(12):3122-3143.
Lupoli et al., "Transpeptidase-mediated incorporation of D-Amino Acids into bacterial peptidoglycan," (2011) J. Am. Chem. Soc. 133(28):10748-10751.
Merkel et al., "Blue Fluroescent Amino Acids as In Vivo Building Blocks for Proteins," (2010) Chembiochem. 11:305-314.
Mobley et al., "Insertion and Fate of the Cell Wall in Bacillus subtilis," (1984) J. Bacteriol. 158(1):169-179.
The Molecular Probes® Handbook, 11th Edition (2010), Chapter 1, "Fluorophores and Their Amine-Reactive Derivatives," 87 pages.
The Molecular Probes® Handbook, 11th Edition (2010), Chapter 3, "Click Chemistry and Other Functional Group Modifications," 29 pages.
Muller et al., "Isotope-Tagged Cross-Linking ReagenReagents. A New Tool in Mass Spectrometric Protein Interaction Analysis," (2001) Anal. Chem. 73:1927-1934.
Nagy et al., "Clickable Long-Wave 'Mega-Stokes' Fluorophore for Orthogonal Chemoselective Labeling of Cells," (2010) Chem. Asian J. 5:773-777.
Nessen et al., "Selective Enrichment of Azide-Containing Peptides from Complex Mixtures," (2009) J. Proteome Res. 8(7):3702-3711.
Neumann et al., "Encoding multiple unnatural amino acids via evolution of a quadruplet-decoding ribosome," (2010) Nature 464:441-4-44.
Olrichs et al., "A Novel in vivo Cell-Wall Labeling Approach Sheds New Light on Peptidoglycan Synthesis in *Escherichia coli*," (2011) Chembiochem 12:1124-1133.
Petrotchenko et al., "Isotopically Coded Cleavable Cross-linker for Studying Protein-Protein Interaction and Protein Complexes," (2005) Mol. Cell. Proteomics 4:1167-1179.
Prescher et al., "Chemistry in living systems," (2005) Nat. Chem. Biol. 1(1):13-21.

Riester et al., "Members of the histone deacetylase superfamily differ in substrate specificity towards small synthetic substrates," Biochem. and Biophys. Res. Comm. (2004) 324(3):1116-1123.
Rippka et al., "Division Patterns and Cellular Differentiation in Cyanobacteria," (1985) Ann. Int. Pasteur/Microbiol. 136A:33-39.
Rostovtsev et al., "A Stepwise Fluisgen Cycloaddition Process: Copper(I)-Catalyzed Regioselective 'Ligation' of Azides and Terminal Alkynes," (2002) angew. Chem. Int. Ed. 41:2596-2599.
Sadamoto et al., "Control of Bacteria Adhesion by Cell-Wall Engineering," (2004) J. Am. Ehcm. Soc. 126:3755-3761.
Saxon et al., "Cell Surface Engineering by a Modified Staudinger Reaction," (2000) Science 287:2007-2010.
Schleifer et al., "Peptidoglycan Types of Bacterial Cell Walls and their Taxonomic Implications," (1972) Bacteriological Reviews 36(4):407-477.
Schneider et al., "NIH Image to ImageJ: 25 years of image analysis," (2012) Nat. Meth. 9(7):671-675.
Schouten et al., "Fluorescent reagents for in vitro studies of lipid-linked steps of bacterial peptidoglycan biosynthesis: derivatives of UDPMurNAc-pentapeptide containing D-systeine at position 4 or 5," (2006) Mol. BioSyst. 2:484-491.
Sham et al., "Essential PcsB putative peptidoglycan hydrolase interacts with the essential FtsXSpn cell division protein in *Streptococcus pneumoniae* D39," (2011) Proc. Natl. Acad. Sci. USA 108(45):E1061-1069.
Shapiro et al., "Specific Assay for Differentiation in the Stalked Bacterium Caulobacter crescentus," (1970) Proc. Natl. Acad. Sci. USA 67(1):200-203.
Simo et al., "Application of stepwise discriminant analysis to discriminant analysis to classify commerical orange juices using chiral micellar electrokinetic chromatography-laser induced fluorescence data of amino acids," (2004) Electrophoresis 25:2885-2891.
Sinz et al., "Mapping spatial proximities of sulfydryl groups in proteins using a fluorogenic cross-linker and mass spectrometry," (2004) Anal. Biochem. 331:27-32.
Sinz et al., "Mapping Protein Interfaces with a Fluorogenic Cross-Linker and Mass Spectrometry: Application to Nebulin-Calmodulin Complexes," (2001) Biochemistry 40:7903-7913.
Staley et al., "Deoxyribonucleic Acid Base Composition of Prosthecomicrobium and Ancalomicrobium Strains," (1973) Intl. J. System. Bacteriol. 23(3):271-273.
Stanier et al., "Purification and Properties of Unicellular Blue-Green Algae (*Order chroococcales*)," (1971) Bacteriol. Rev. 35(2):171-205.
Subach et al., "A photoswitchable orange-to-far-red fluorescent protein, PSmOrange," (2011) Nature Methods 8(9):771-777.
Tang et al., "Mass Spectrometry Identifiable Cross-Linking Strategy for Studying Protein-Protein Interactions," (2005) Anal. Chem. 77:311-318.
Tiyanont et al., "Imaging peptidoglycan biosynthesis in Bacillus subtilis with fluorescent antibiotics," (2006) Proc. Natl. Acad. Sci. USA 103(29):11033-11038.
Tornoe et al,. "Peptidotriazoles on Solid Phase: [1,2,3]-Triazoles by Regiospecific Copper(I)-Catalyzed 1,3-Dipolar Cycloadditions of Terminal Alkynes to Azides," (2002) J. Org. Chem. 67:3057-3064.
Trester-Zedlitz et al., "A Modular Cross-Linking Approach for Exploring Protein Interactions," (2003) J. Am. Chem. Soc. 125:2416-2425.
Trnka et al., "Topographic Studies of the GroEL-GroES Chaperonin Complex by Chemical Cross-linking Using Diformyl Ethynylbenzene," (1010) Mol. Cell. Proteomics 9:2306-2317.
Typas et al., "From the regulation of peptidoglycan synthesis to bacterial growth and morphology," (2012) Nat. Rev. Microbiol. 10:123-136.
van Dam et al., "Specific Labeling of Peptidoglycan Precursors as a Tool for Bacterial Cell Wall Studies," (2009) Chembiochem. 10:617-624.
Vellucci et al., "Selective Enrichment and Identification of Azide-tagged Cross-Linked Peptides Using Chemical Ligation and Mass Spectrometry," (2010) J. Am. Soc. Mass. Spectrom. 21:1432-1445.

(56) References Cited

OTHER PUBLICATIONS

Vinatier et al., "In vitro biosynthesis of bacterial peptidoglycan using D-Cys-containing precursors: fluorescent detection of transglycosylation and transpeptidation," (2009) Chem. Commun. 27:4037-4039.
Wang et al., "Expanding the Genetic Code of *Escherichia coli*," (2001) Science 292:498-500.
Wine et al., "Identification of Components of Protein Complexes Using a Fluorescent Photo-Cross-Linker and Mass Spectrometry," (2002) Anal. Chem. 74:1939-1945.
Yang et al., "Monovalent, Clickable, Uncharged, Water-Soluble Perylenediimide-Cored Dendrimers for Target-Specific Fluorescent Biolabeling," (2011) J. Am. Chem. Soc. 133:9964-9967.
Young, Kevin D., "The Selective Value of Bacterial Shape," (2006) Microbiol. Mol. Biol. Rev. 70(3):660-703.
Zapun et al., "The different shapes of cocci," (2008) FEMS Microbiol. Rev. 32:345-360.
Non-Final Office Action dated May 26, 2017 for U.S. Appl. No. 14/395,815, 14 pages.
Janssen (Development and perspectives of fluorescent receptor assays: A case study with Benzodiaepines, 1997).
Kim et al., (Bioconjug Chem. Mar. 2008); 19(3): 786-791).
Atdbio Alexa dyes (download from http://www.atdbio.com/content/34/Alexa-dyes on Apr. 20, 2017).
Scienceforms.net (http://www.scienceforums.net/topic/16789-positivenegative-controls/, Feb. 13, 2006).
Final Office dated Feb. 15, 2018 for U.S. Appl. No. 14/395,815, 27 pages.
Non-Final Office Action dated Jun. 20, 2018 for U.S. Appl. No. 14/395,815, 25 pages.
Non-Final Office Action dated Oct. 9, 2015 for U.S. Appl. No. 14/395,815, 11 pages.
Final Office Action dated Jun. 30, 2016, for U.S. Appl. No. 14/395,815, 13 pages.

\* cited by examiner

*B. subtilis ΔdacA*

*A. tumefaciens*

| Strain and treatment | Modified PG |
|---|---|
| B. subtilis ΔdacA + HADA | 2.1% |
| B. subtilis wt + NADA | 0.2% |
| E. coli + HADA | 2.8% |
| E. coli + NADA | 1.9% |
| A. tumefaciens + HADA | 2.5% |

FIG. 9C

*Escherichia coli*

*Bacillus subtilis ΔdacA*

(i)  (ii)

COMPOSITIONS FOR IN SITU LABELING OF BACTERIAL CELL WALLS WITH FLUOROPHORES AND METHODS OF USE THEREOF

CROSS-REFERENCE TO RELATED APPLICATIONS

The present application is a continuation of U.S. patent application Ser. No. 14/395,815, filed Oct. 20, 2014, which is the National Stage of International Application No. PCT/US13/37504, filed Apr. 21, 2013, and entitled "COMPOSITIONS FOR IN SITU LABELING OF BACTERIAL CELL WALLS WITH FLUOROPHORES AND METHODS OF USE THEREOF," which claims benefit of priority under 35 U.S.C. 119 to U.S. provisional patent application Ser. No. 61/636,640, filed Apr. 21, 2012, and entitled "COMPOSITIONS FOR COVALENTLY LABELING BACTERIAL CELL WALLS WITH FLUOROPHORES AND METHODS OF USE," and U.S. provisional patent application Ser. No. 61/718,048, filed Oct. 24, 2012, and entitled "COMPOSITIONS FOR IN SITU LABELING OF BACTERIAL CELL WALLS WITH FLUOROPHORES AND METHODS OF USE THEREOF," the contents of both which are herein incorporated by reference in their entireties.

STATEMENT REGARDING FEDERALLY SPONSORED RESEARCH OR DEVELOPMENT

This invention was made with government support under AI059327 and GM051986 awarded by the National Institutes of Health. The government has certain rights in the invention.

FIELD OF THE INVENTION

The invention relates generally to microbiology, and more particularly to compositions and methods for assessing cell wall synthesis in bacteria, for identifying bacteria, and for screening for cell wall-acting/-disrupting agents.

BACKGROUND

Bacterial growth is controlled by the domain-specific peptidoglycan (PG) cell wall, a rigid and essential structure composed of glycan strands cross-linked by D-amino acid (DAA)-containing short peptides, whose biosynthesis machinery is a target for antibiotics.

Despite the importance of PG, knowledge of its dynamics has been severely hampered by lack of a strategy for direct imaging of sites of PG biosynthesis in live cells. Significant limitations of current labeling methods, such as toxic effects and poor membrane permeability of the probes, have limited their applicability to only a small set of bacterial species. Moreover, these methods are labor-intensive and their sensitivity suffers from their indirect and multiple-step nature.

Methods relying on fluorescently labeled antibiotics to study bacterial cell wall synthesis and to discover new antibiotics to which bacteria remain susceptible have had a profound impact on the field. The current methods, however, have at least two inherent limitations. First, antibiotic concentration needs to be carefully controlled to avoid damage to the cell. Second, because these agents bind to specific sites on cell surfaces, they only will appear at sites of active PG biosynthesis.

For the foregoing reasons, there is a need for additional compositions and methods for assessing PG biosynthesis in bacteria and for discovering bacterial cell wall-acting/-disrupting agents that can be used to treat infections caused by multidrug-resistant bacteria.

BRIEF SUMMARY

In a first respect, a modified amino acid is disclosed that includes a D-amino acid covalently attached to a fluorescent label.

In a second respect, a muramylpentapeptide precursor unit is disclosed that includes an N-acetyl muramic acid (NAM) moiety having a stem peptide of three to five amino acids. One or more of the amino acids in the stem peptide includes a modified amino acid that includes a D-amino acid covalently attached to a fluorescent label and optionally an additional modified amino acid. The additional modified amino acid includes a clickable D-amino acid.

In a third respect, a peptidoglycan unit is disclosed that includes a muramylpentapeptide precursor unit as described above in the second respect that is covalently linked to an N-acetyl glucosamine (NAG) moiety.

In a fourth respect, a method of assessing bacterial cell wall synthesis in real time is described. The method includes the step of providing live bacteria with a first amount of at least one modified amino acid comprising a D-amino acid covalently attached to a fluorescent label, and optionally a second amount of at least one additional modified amino acid comprising a clickable D-amino acid, under conditions sufficient for bacterial cell wall synthesis. The bacteria covalently incorporate the at least one modified amino acid and optionally the at least one additional modified amino acid into a stem peptide of peptidoglycan of the bacterial cell wall.

In a fifth respect, a method of screening for a putative cell wall-acting agent is disclosed. The method includes the step of co-contacting bacteria with an effective amount of an agent and an amount of at least one modified amino acid comprising a D-amino acid covalently attached to a fluorescent label, and optionally an amount at least one additional modified amino acid comprising a clickable D-amino acid, under conditions sufficient to permit ongoing peptidoglycan biosynthesis in a bacterial cell wall. The agent comprises a cell wall-acting agent if the agent interferes with ongoing peptidoglycan biosynthesis in the bacterial cell wall.

In a sixth respect, a method of screening for a putative cell wall-disrupting agent is disclosed. The method includes the step contacting modified bacteria with an amount of an agent. The agent is a cell wall-disrupting agent if the agent weakens integrity of peptidoglycan in an existing bacterial cell wall. In this method, the modified bacteria have a modified cell wall containing modified peptidoglycan having at least one stem peptide containing at least one modified amino acid comprising a D-amino acid covalently attached to a fluorescent label, and optionally at least one additional modified amino acid comprising a clickable D-amino acid.

In a seventh respect, a method of identifying bacteria is disclosed. The method includes two steps. The first step includes contacting live bacteria with an amount of at least one modified amino acid comprising a D-amino acid covalently attached to a fluorescent label, and optionally an amount of at least one additional modified amino acid comprising a clickable D-amino acid, under conditions sufficient for ongoing bacterial cell wall synthesis. The bacteria covalently incorporate into peptidoglycan of a bacterial cell wall the at least one modified amino acid, and optionally the at least one additional modified amino acid.

Each of the least one modified amino acid and optionally the at least one additional modified amino acid comprises a spectrally distinct fluorescent label. The second step includes visualizing the spectrally distinct fluorescent labels to determine an incorporation pattern of the at least one modified amino acid, and optionally the at least one additional modified amino acid, wherein the incorporation pattern identifies the bacteria.

In an eighth respect, a kit for incorporating labeled D-amino acids into live bacteria is disclosed. The kit includes at least one modified amino acid comprising a D-amino acid covalently attached to a fluorescent label and a positive bacterial control. The kit can include an optional negative bacterial control. The positive bacterial control has at least one modified amino acid comprising a D-amino acid covalently attached to a fluorescent label incorporated into a stem peptide of peptidoglycan of the bacterial cell wall. The optional negative bacterial control, if included, does not have the modified amino acid comprising a D-amino acid covalently attached to a fluorescent label incorporated into a stem peptide of peptidoglycan of the bacterial cell wall.

These and other features, objects and advantages of the present invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

The features, objects and advantages other than those set forth above will become more readily apparent when consideration is given to the detailed description below. Such detailed description makes reference to the following drawings.

FIGS. 9A-D show FDAA incorporation into the stem peptide of the PG unit.

FIG. 9A shows a schematic representing the muramylpentapeptide precursor as incorporated into a nascent PG unit and a modified D-amino acid (FDAA).

FIG. 9B shows HPLC detection of modified muropeptides in *E. coli* incubated with HADA, HALA and NADA, or NALA. Samples were monitored using a dual wavelength UV monitor set for general muropeptide detection and for FDAA-specific wavelengths. Peaks HEC-1 (panel (i)) and NEC-1 (panel (ii)) correspond to the HADA- or NADA-modified muropeptides in *E. coli* that were further characterized by electrospray ionization MS/MS (ESI-MS/MS).

FIG. 9C shows percentage of FDAA incorporation into the total muropeptides varies among bacteria as revealed by HPLC analysis.

FIG. 9D shows a schematic representing MS/MS analyses of FDAAs exclusively incorporated into the 5th position in *B. subtilis* (panel (i)) and the 4th position of muropeptides in *E. coli* and *A. tumefaciens* (panel (ii)).

FIG. 10A shows time-lapse microscopy of HADA-labeled *E. coli* and *B. subtilis* ΔdacA cells imaged during growth on LB agarose pads.

FIG. 10B shows super-resolution microscopy of *E. coli* after short pulses with HADA (panels (i) and (ii)).

FIG. 10C show super-resolution microscopy of *A. tumefaciens* after short pulses with HADA.

FIG. 10D shows super-resolution microscopy of *S. aureus* after a short pulse with HADA. Autofluorescence is shown in red.

FIG. 10E shows triple labeling of *A. tumefaciens* with HADA (blue), EDA (clicked with red sulfo-Cy3-azide) and NADA (green).

FIG. 10F shows triple labeling of *S. venezuelae* with NADA (green), TDL (red) and HADA (blue).

Figure 1:
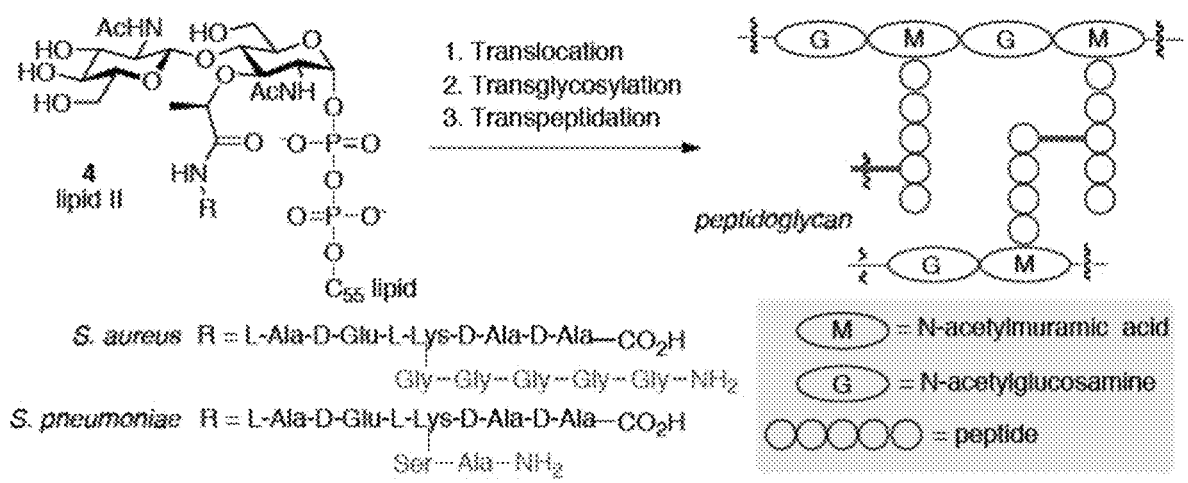
FIG. 1 shows the three general stages of PG biosynthesis and general structures of the NAM and NAG units of PG.
Figure 2:
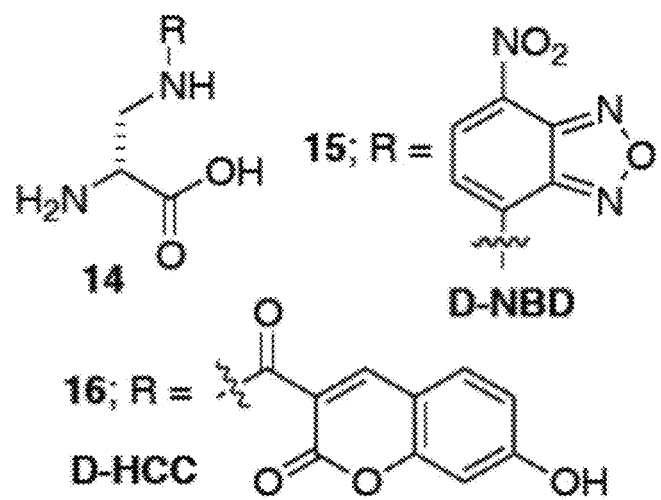
FIG. 2 shows exemplary D-Ala-based FDAAs. D-NBD and D-HCC (based on (R)-diaminopropionic acid) emit in the green and blue regions, respectively.

While the present invention is amenable to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments and claims herein for interpreting the scope of the invention.

DETAILED DESCRIPTION

The compositions and methods now will be described more fully hereinafter with reference to the accompanying drawings, in which some, but not all permutations and variations of embodiments of the invention are shown. Indeed, the invention may be embodied in many different forms and should not be construed as limited to the embodiments set forth herein. These embodiments are provided in sufficient written detail to describe and enable one skilled in the art to make and use the invention, along with disclosure of the best mode for practicing the invention, as defined by the claims and equivalents thereof.

Likewise, many modifications and other embodiments of the compositions and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

Overview

Previous efforts to label PG in live bacteria principally have relied upon cell wall-active antibiotics (e.g., vancomycin, ramoplanin) modified with fluorophores or cell wall precursors/substrates covalently modified with fluorescent reporter groups. The compositions and methods described herein, however, take advantage of mechanisms for incorporating labeled DAAs into the stem peptides displayed on a bacterial cell wall surface.

The work described herein demonstrates how to make derivatized DAA having a suitable label, such as an appropriate fluorophore and how such derivatized compounds can be visualized in live cells by fluorescence microscopy following the incorporation of the derivatized compounds into PG and thus the cell wall. In the range of physiologically relevant concentrations, the incorporated FDAAs do not appear to be toxic to bacteria. Unlike previous methods that employ covalently modified cell wall precursors, the methods described herein do not appear to adversely affect cell morphology. In addition, the methods described herein enable pulse-chase experiments that cannot be easily executed in the presence of fluorescently-modified cell wall active drugs. Because the disclosed derivatized compounds have low or minimal toxicity to live cells, they are ideal markers to evaluate and screen microbiostatic or microbiotoxic compounds that do adversely affect microorganism growth and viability, such as studies directed to development of novel antibiotics.

Studies disclosed herein demonstrate that the compositions and methods are applicable to a wide array of Gram-positive and Gram-negative bacteria and provides significant utility for probing PG biosynthesis, cell wall morphogenesis and the response of the PG biosynthetic machinery to cell wall-active agents and/or cell wall-disrupting agents. The present disclosure therefore provides compositions and methods for studying bacterial cell wall PG biosynthesis and for discovering bacterial cell wall-acting and/or cell wall-disrupting agents.

Compositions

Fluorescent D-Amino Acids (FDAAs)

Compositions of the invention include labeled D-amino acids (DAAs), especially fluorescent D-amino acids (FDAAs). As used herein, "amino acid" or "amino acid residue" are used interchangeably to mean a molecule containing a first, or alpha, carbon attached to an amine group, a carboxylic acid group and a side-chain that is specific to each amino acid. A natural amino acid can include conventional elements such as carbon, hydrogen, oxygen, nitrogen and sulfur. An amino acid may be a naturally occurring amino acid or artificially-created unnaturally occurring amino acid. Preferably, the amino acid is naturally occurring, and, unless otherwise limited, may encompass known analogues/synthetics of natural amino acids that can function in a similar manner as naturally occurring amino acids. With the exception of glycine, the natural amino acids all contain at least one chiral carbon atom. These amino acids therefore exist as pairs of stereoisomers (D- and L-isomers). Of particular interest herein are D-isomers or D-amino acids, particularly D-Ala, D-Asp, D-Cys, D-Glu and D-Lys, which are frequently found in the stem peptide of the PG unit.

It is well known in the art that amino acids within the same conservative group typically can substitute for one another without substantially affecting the function of a protein. For the purpose of the present disclosure, such conservative groups are set forth in Table 1 and are based preferably on shared properties, as readily appreciated to those skilled in the art. See also, Alberts et al., "Small molecules, energy, and biosynthesis" 56-57 In: Molecular Biology of the Cell (Garland Publishing Inc. 3$^{rd}$ ed. 1994).

TABLE 1

Amino Acids and Their Conservative Substitutions.

| Residue | Side Chain Polarity | Side Chain pH | Hydropathy Index | Preferred Conservative Substitutions |
| --- | --- | --- | --- | --- |
| Ala (A) | Non-polar | Neutral | 1.8 | Ser |
| Arg (R) | Polar | Basic (strongly) | −4.5 | Lys, Gln |
| Asn (N) | Polar | Neutral | −3.5 | Gln, His |
| Asp (D) | Polar | Acidic | −3.5 | Glu |
| Cys (C) | Non-polar | Neutral | 2.5 | Ser |
| Gln (Q) | Polar | Neutral | −3.5 | Asn, Lys |
| Glu (E) | Polar | Acidic | −3.5 | Asp |
| Gly (G) | Non-polar | Neutral | −0.4 | Pro |
| His (H) | Polar | Basic (weakly) | −3.2 | Asn, Gln |
| Ile (I) | Non-polar | Neutral | 4.5 | Leu, Val |
| Leu (L) | Non-polar | Neutral | 3.8 | Ile, Val |
| Lys (K) | Polar | Basic | −3.9 | Arg, Gln |
| Met (M) | Non-polar | Neutral | 1.9 | Leu, Ile |
| Phe (F) | Non-polar | Neutral | 2.8 | Met, Leu, Tyr |
| Pro (P) | Non-polar | Neutral | −1.6 | Gly |
| Ser (S) | Polar | Neutral | −0.8 | Thr |

TABLE 1-continued

Amino Acids and Their Conservative Substitutions.

| Residue | Side Chain Polarity | Side Chain pH | Hydropathy Index | Preferred Conservative Substitutions |
|---|---|---|---|---|
| Thr (T) | Polar | Neutral | −0.7 | Ser |
| Trp (W) | Non-polar | Neutral | −0.9 | Tyr |
| Tyr (Y) | Polar | Neutral | −1.3 | Trp, Phe |
| Val (V) | Non-polar | Neutral | 4.2 | Ile, Leu |

The following six groups each contain amino acids that are typical but not necessarily exclusive conservative substitutions for one another: 1) Alanine (A), Serine (S) and Threonine (T); 2) Aspartic acid (D) and Glutamic acid (E); 3) Asparagine (N) and Glutamine (Q); 4) Arginine (R) and Lysine (K); 5) Isoleucine (I), Leucine (L), Methionine (M), and Valine (V); and 6) Phenylalanine (F), Tyrosine (Y) and Tryptophan (W).

Examples of suitable labels for the DAAs include, but are not limited to, radiolabels, biotin (which may be detected by avidin or streptavidin conjugated to peroxidase), lanthanides, alkaline phosphatase and fluorescent labels (e.g., coumarins, fluoresceins, cyanines, bodipy dyes, green fluorescent protein, quantum dots rhodamine, especially the Alexa Fluor® family of fluorescent dyes available from Invitrogen/Molecular Probes). Other labels amenable for use in the modified D-amino acids disclosed herein include metals and isotopic labels.

Labeling of DAAs can be carried out by covalently attaching the label to a free amine group, such as free amine groups present on the side-chain that is specific to each amino acid. If the side chain lacks a free amine group, one of skill in the art understands how to add such groups, as is the case of adding such a group to D-Ala to obtain 3-amino-D-Ala. Some labels can be detected by using a labeled counter suitable for the detection of the label in question. In the Examples below, 7-hydroxycoumarin 3-carboxylic acid (HCC—OH), 7-nitrobenzofurazan (NBD), 4-chloro-7-nitrobenzofurazan (NBD-Cl), fluorescein (F) and carboxytetramethylrhodamine (T) were covalently attached to DAAs as labels.

Other coupling chemistries are known in the art that can be used for introducing labels into amino acids having functional groups other than an amine. Such amino acids include a functional alcohol group (e.g., serine and tyrosine), thiol group (e.g., cysteine), or carbonyl or carboxylate group (e.g., aspartate and glutamate). Such functional groups can be derivatized or reacted with suitably modified, activated coupling agents having labels of the types disclosed herein.

An example of a FDAA includes HADA, which is a HCC—OH-labeled 3-amino-D-Ala. Another example of a FDAA includes NADA, which is a NBD-Cl-labeled 3-amino-D-Ala. Another example includes FDL, which is a F-labeled D-Lys. Another example is TDL, which is a T-labeled D-Lys. Another example includes HDL, which is a HCC—OH-labeled D-Lys. Another example includes NDL, which is a NBD-Cl-labeled D-Lys. Another example includes FADA, which is a F-labeled 3-amino-D-Ala. Another example includes TADA, which is a T-labeled 3-amino-D-Ala. Other FDAAs can include a D-Glu having its side chain modified to include a free amine group linked to any of the fluorescent labels above (e.g., HADG, NADG, FADG and TADG).

Figure 7:
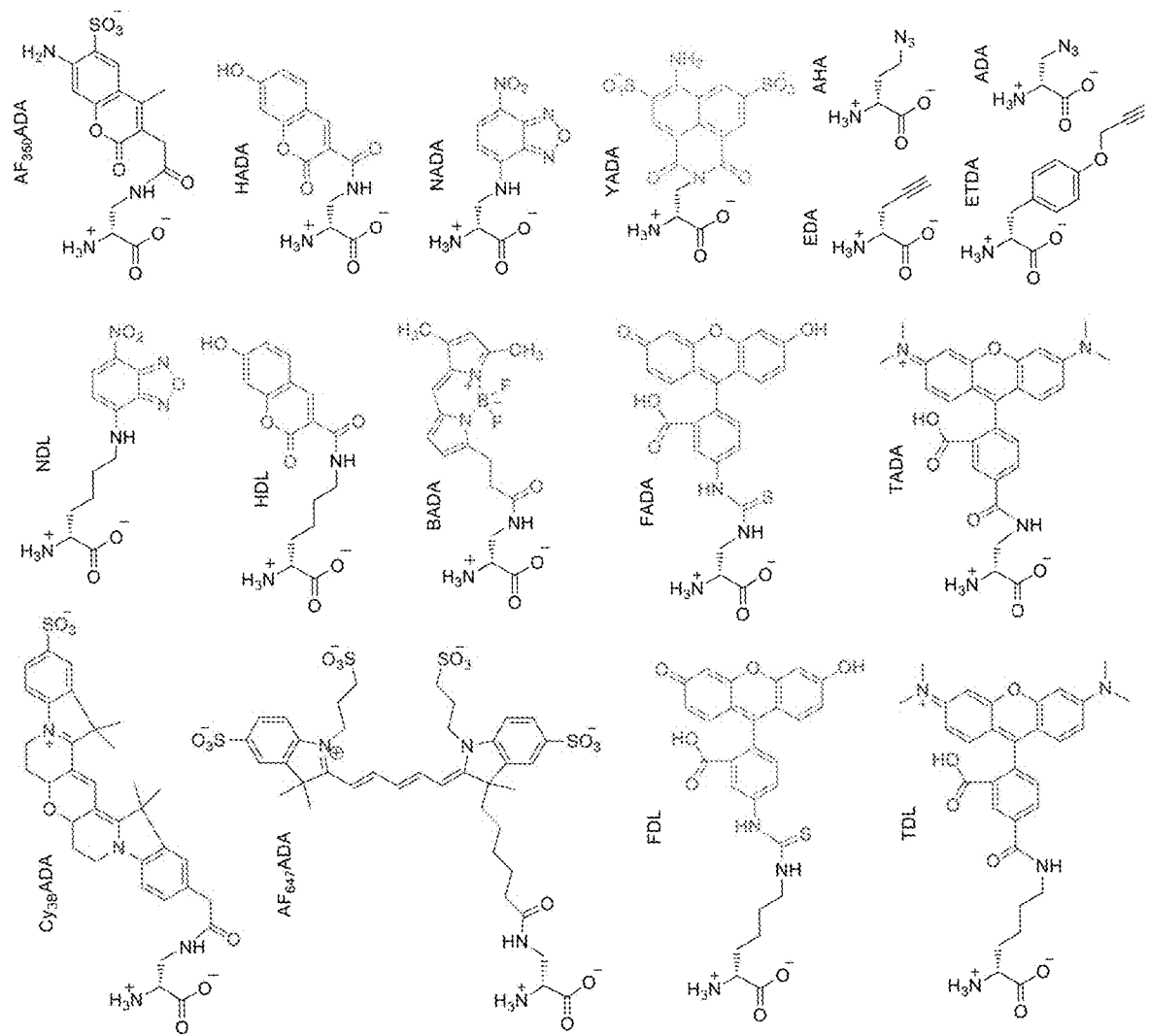
FIG. 7 shows exemplary structures for FDAAs, such as HCC—OH-labeled 3-amino-D-Ala (HADA), NBD-Cl-labeled 3-amino-D-Ala (NADA), F-labeled D-Lys (FDL) and T-labeled D-Lys (TDL), as well as exemplary structures for CDAAs, such as EDA and ADA.

See, e.g., FIG. 7, for other examples of preferred labels and modified FDAAs.

Methods of fluorescently labeling and detecting amino acids are well known in the art. See, Braun & Dittrich (2010) *Beilstein J. Org. Chem.* 6:69; Katritzky & Narindoshvili (2009) *Org. Biomol. Chem.* 7:627-634; Merkel et al. (2010) *Chembiochem.* 11:305-314; Cava et al. (2011) *Cell Mol. Life Sci.* 68:817-831; Lam et al. (2009) *Science* 325:1552-1555; Cava et al. (2011) *EMBO J.* 30:3442-3453; and Lupoli et al. (2011) *J. Am. Chem. Soc.* 133:10748-10751.

Clickable D-Amino Acids (CDAA's)

Compositions of the invention also include clickable D-amino acids (CDAAs). The CDAAs have a DAA backbone that includes, for example, an alkyne or azide functional group present on the side-chain that is specific to each amino acid that can be captured in situ by a labeled, detecting agent carrying a conjugate functional group via click-chemistry. Functional groups in a DAA backbone that can be targeted by the labeled, detecting agent include, but are not limited to, primary amines, carboxyls, sulfhydryls, carbohydrates and carboxylic acids.

One of skill in the art is familiar with "click" chemistry, which utilizes chemical cross-linking agents to add functional groups to molecules. See, Kolb et al. (2001) *Angew. Chem. Int. Ed.* 40:2004-2021; and Evans (2007) *Aust. J. Chem.* 60:384-395.

Cross-linking and enrichment strategies for separating a cross-linking reaction from enrichment steps have been developed based on bioorthogonal chemistries including the azide-alkyne "click" cycloaddition and Staudinger ligation using alkyne- or azide-labeled cross-linking agents (e.g., fluorescent labels). Azides and alkynes are not naturally found in proteins, peptides, nucleic acids or glycans; therefore, these moieties can be engineered onto the DAAs and labeled, detecting agent to generate azide-containing molecules and alkyne-containing molecules that are reactive with one another. As such, the orthogonality of azides and alkynes to biological processes (e.g., competing reactions) is a significant advantage of these methods. Moreover, "click" cycloadditions can be performed under aqueous conditions, allowing enrichment by conjugation of an appropriate affinity or labeling tag. See, generally, Rostovtsev et al. (2002) *Angew. Chem. Int. Ed.* 41:2596-2599; Tornoe et al. (2002) *J. Org. Chem.* 67:3057-3064; Baskin et al. (2007) *Proc. Natl. Acad. Sci. USA* 104:16793-16797; Saxon et al. (2000) *Science* 287:2007-2010; Chowdhury et al. (2009) *Anal. Chem.* 81:5524-5532; Trnka & Burlingame (2010) *Mol. Cell. Proteomics* 9:2306-2317; Nessen et al. (2009) *J. Proteome Res.* 8:3702-3711; Vellucci et al. (2010) *J. Am. Soc. Mass Spectrom.* 21:1432-1445; and Jewett & Bertozzi (2010) *Chem. Soc. Rev.* 39:1272-1279. See also, Int'l Patent Application Publication No. WO 2012/006603. As used herein, "click chemistry" and "clickable" therefore mean a reaction between azide-containing molecules and alkyne-containing molecules to yield a covalent product-1,5-disubstituted 1,2,3-triazole. The reaction can be a copper(I)-catalyzed alkyne azide cycloaddition (CuAAC) or, in cases where copper toxicity may be an issue, can be a copper(I)-free-catalyzed alkyne azide cycloaddition.

Examples of functional groups for use on azide-containing molecules and alkyne-containing molecules include, but are not limited to, hexynyl groups, pentynyl groups, heptynyl groups, azido-propyl groups, azido-butyl groups and azido-pentyl groups. When the functional group of alkyne-containing molecules (e.g., DAAs) is an alkynyl group (e.g., hexynyl, pentynyl or heptynyl), the functional group of azide-containing molecules (e.g., labeled, detecting agents) has the corresponding clickable azido group. Likewise, when the functional group of azide-containing molecules (e.g., DAAs) is an azide group (e.g., azido-propyl, azido-butyl, or azido-pentyl), the functional group of alkyne-containing molecules (e.g., labeled, detecting agents) has the corresponding clickable alkynyl group.

As such, various labeling designs for detecting agents are known including, but not limited to, biotinylated agents, isotope-coded agents, fluorophore-labeled agents, mass-tag-labeled agents and chromophore-labeled agents. It is also known that the addition of functional groups can cause the cross-linker to become very bulky or less cell-permeable, and thus not very effective for in vivo and/or in situ cross-linking. To reduce the total size of the cross-linker, separation of the cross-linking step from conjugation of affinity tags can be one effective strategy. See, Trester-Zedlitz et al. (2003) J. Am. Chem. Soc. 125:2416-2425; Tang et al. (2005) Anal. Chem. 77:311; Kang et al. (2009) Rapid Commun. Mass Spectrom. 23:1719-1726; Chu et al. (2006) J. Am. Chem. Soc. 128:10362-10636; Muller et al. (2001) Anal. Chem. 73:1927-1934; Collins et al. (2003) Bioorg. Med. Chem. Lett. 13:4023-4026; Petrotchenko et al. (2005) Mol. Cell. Proteomics 4:1167-1179; Wine et al. (2002) Anal. Chem. 74:1939-1945; Sinz et al. (2001) Biochemistry 40:7903-7913; and Sinz & Wang (2004) Anal. Biochem. 331:27-32.

In some instances, the detecting agents, whether having an alkynyl or azido functional group, can be fluorophore-labeled. Examples of fluorophores include, but are not limited to, Alexa Fluor® dyes, BODIPY® dyes, fluorescein, Oregon Green® 488 and Oregon Green® 514 dyes, Rhodamine Green and Rhodamine Green-X dyes, eosin, tetramethylrhodamine, Lissamine Rhodamine B and Rhodamine Red-X dyes, X-Rhodamine, Texas Red® and Texas Red®-X dyes, naphthofluorescein, Carboxyrhodamine 6G, QSY dyes: fluorescence quenchers, nonfluorescent malachite green, coumarin derivatives, Pacific Orange dye, cascade blue and other pyrene derivatives, cascade yellow and other pyridyloxazole derivatives, naphthalenes (e.g., dansyl chloride), dapoxyl dye, bimane, 1-dimethylamine-N(2-azido-ethyl) naphthalene-5-sulfonamide, 6-(6-amino-2-(2-azido-ethyl)1,3-dioxo-1H-benzo(de)-2(3H)isoquinoline, 6-(6-amino-2-(2-propinyl)1,3-dioxo-1H-benzo(de)-2(3H) isoquinoline, 8-(4-azidoethyloxyphenyl)-2,6-diethyl-1,3,5,7-tetramethyl-4,4-difluoro-4-bora-3a,4a-diaza-s-indacene, 8-(4-propynyloxyphenyl)-2,6-diethyl-1,3,5,7-tetramethyl-4,4-difluoro-4-bora-3a,4a-diaza-s-indacene, 1-(3-azido-propoxy)-7-methylamino-phenoxazin-3-one, 1-(2-propy-nyl)-7-methylamino-phenoxazin-3-one, N-(5-(3-azidopropylamino)-9H-benzo(a)-phenoxazin-9-ylidene)-N-methyl-methanaminium chloride, N-(5-(3-propynyl-amino)-9H-benzo(a)-phenoxazin-9-ylidene)-N-methyl-methanaminium chloride, (9-(3-azido-propoxy)-7-piperidin-1-yl-phenoxazin-3-ylidene)-dimethyl-ammonium perchlorate. See also, Kele et al. (2009) Org. Biomol. Chem. 7:3486-3490; Nagy et al. (2010) Chem. Asian J. 5:773-777; Filnov et al. (2011) Nat. Biotechnol. 29:757-761; Subach et al. (2011) Nature Methods 8:771-777; Yang et al. (2011) J. Am. Chem. Soc. 133:9964-9967; Zin (2011) Nature Methods 8:726-728; and "Fluorophores and their amine-reactive derivatives," Chapter 1 and "Click Chemistry and other functional group modifications," Chapter 3 in The Molecular Probes® Handbook (available on the World Wide Web at invitrogen.com/site/us/en/home/References/Molecular-Probes-The-Handbook.html). A variety of clickable fluorophores are commercially available from, for example Sigma Aldrich, Active Motif Chromeon and Invitrogen/Molecular Probes. In the examples below, CDAAs were clicked with red sulfo-Cy3-azide.

An example of a CDAA includes EDA. Another example of a CDAA includes ADA. See, e.g., FIG. 7.

Fluorescent Muramylpentapeptide Precursor Units (FMPUs)

Figure 9A:
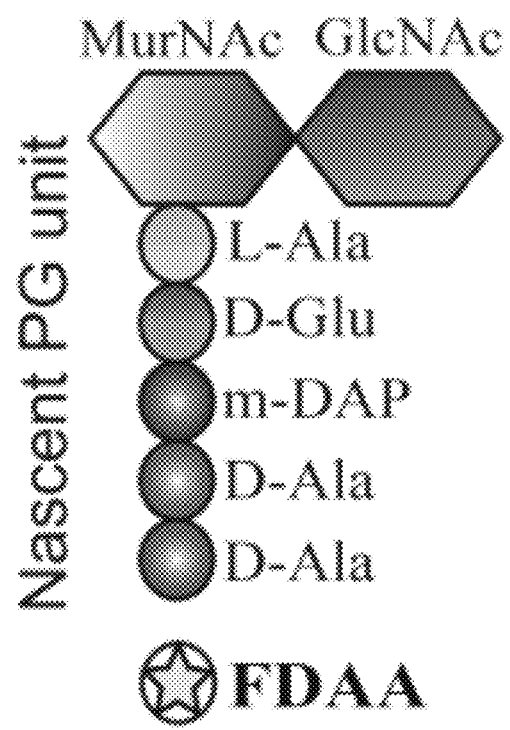

Compositions of the invention also include fluorescent muramylpentapeptide precursor units (FMPUs) having an NAM moiety with a peptide chain of three to five amino acids in which one or more of the amino acids in the stem peptide are FDAAs and/or CDAAs as described herein. See, e.g., FIGS. 9A and 9D.

Fluorescent Peptidoglycan Units (FPGUs)

Compositions of the invention also include fluorescent peptidoglycan units (FPGUs). The FPGUs have a FMPU as described herein linked to a NAG moiety. See, e.g., FIGS. 9A and 9D.

Bacterial Cells Having Fluorescent D-Amino Acids

Compositions of the invention also include live bacteria having FDAAs, CDAAs, FMPUs and/or FPGUs as described herein incorporated into PG in a cell wall.

While Gram-positive bacteria tend to have a thicker PG layer, it is intended that the bacteria can be Gram-positive bacteria or Gram-negative bacteria. Examples of suitable Gram-positive bacteria include, but are not limited to, *Actinomyces* spp., *Bacillus* spp., *Brachybacterium* spp., *Clostridium* spp., *Corynebacterium* spp., *Diplococcus* spp., *Enterococcus* spp., *Lactococcus* spp., *Listeria* spp., *Nocardia* spp., *Propionibacterium* spp., *Staphylococcus* spp., *Streptococcus* spp. *Streptomyces* spp. In the examples below, live *B. subtilis*, *B. conglomeratum*, *L. lactis*, *S. aureus*, *S. pneumoniae*, *S. venezuelae*, were grown in the presence of FDAAs and/or CDAAs.

Examples of suitable Gram-negative bacteria include, but are not limited to, *Acinetobacter* spp., *Agrobacterium* spp., *Bordetella* spp., *Borrelia* spp., *Brucella* spp., *Burkholderia* spp., *Campylobacter* spp., *Caulobacter* spp., *Chlamydia* spp., *Enterobacter* spp., *Escherichia* spp., *Helicobacter* spp., *Hemophilus* spp., *Klebsiella* spp., *Legionella* spp., *Neisseria* spp., *Proteus* spp., *Pseudomonas* spp, *Salmonella* spp., *Shigella* spp., *Synechocystis* spp., *Verrucomicrobia* spp., *Vibrio* spp. and *Yersina* spp. In the examples below, live *A. tumefaciens, B. phytofirmans, C. crescentus, E. coli, Synechocystis* sp. PCC 6803 and *V. spinosum* were grown in the presence of FDAAs and/or CDAAs.

Kits

Compositions of the invention also include kits having one or more FDAA, CDAA, FMPU and/or FPGU as described herein and optionally one or more labeled detecting agents (if CDAAs are included in the kits) for use in in situ labeling/probing of PG during biosynthesis, as well as for screening for bacterial cell wall-acting and/or cell wall-disrupting agents. The kits also can include additional reagents such as unlabeled DAAs, unlabeled L-amino acids (LAAs) and/or labeled LAAs. The kits also can include positive and/or negative bacterial controls, where the controls have unlabeled DAAs, CDAAs and LAAs or labeled DAAs and LAAs incorporated into PG in a cell wall.

As used herein, "kit" means any manufacture (e.g., a package or a container) having, for example, at least one FDAA and/or CDAA and a positive and/or negative control. The kit may be promoted, distributed, or sold as a unit for performing any of the methods described herein.

Though not necessarily required, kits preferably include instructions, procedures and/or directions that guide users or ones skilled in the art how to use the agents, reagents, and/or other components for their intended purpose. For example, kits can include a package insert describing procedures for carrying out any one of the methods described herein or analytical information for correlating the level of expression measured in live bacteria. Likewise, the package insert can include representative images of positive or negative samples with low or high levels of incorporation as compared to an appropriate control. The kits can be promoted, distributed or sold as units for performing the methods described below.

The kits also can include a receptacle or other means for holding a sample to be evaluated for FDAA and/or CDAA incorporation, and means for determining the presence and/or quantity of FDAA and/or CDAA incorporation in live bacteria.

The kits also can include at least one buffer. Examples of buffers include, but are not limited to, cell isolation buffers, fixation buffers, lysis buffers, permeabilization buffers, sonication buffers, separation buffers, stabilization buffers and wash buffers. Though not limited, buffers include strong acids in combination with weak bases, strong bases in combination with weak acids, a combination of weak acids and bases, or even a small or low concentration (e.g., within the range from about 0.1 mM to about 10 mM) of an acid or base, in the absence of a conventional conjugate base or acid, respectively; typically, however another component of the mixture may provide such conjugate acid or base function. Examples of acids and bases, both in terms of ionization/dissociation strength (i.e., strong or weak) and type (i.e., inorganic or organic), are well known in the art.

Any or all of the kit components can be provided within containers that protect them from the external environment, such as in sealed containers.

Methods

Methods include assessing bacterial cell wall biosynthesis (and PG recycling) in real time. As shown in FIG. 1, bacterial cell wall biosynthesis typically involves three steps: translocation, transglycosylation and transpeptidation. In the translocation and transglycosylation steps, carbohydrate backbone is formed by polymerization via glycosidic bond formation between the C(4)-hydroxyl of a membrane-bound lipid II intermediate and the anomeric center of a membrane-bound glycan strand. Bacterial transpeptidases mediate crosslinking of the resulting elongated glycan strand. The cross-link is installed via attack of an amino group, either from the Lys residue itself or from a short peptide chain appended to the Lys residue, onto the penultimate D-Ala residue of an adjacent pentapeptide strand and results in cleavage of the terminal D-Ala residue. This rigid macromolecular structure, essential to both Gram-negative and Gram-positive bacteria, enables bacterial cells to resist lysis and, subsequently, cell death resulting from high internal osmotic pressure.

These methods typically begin by providing live Gram-positive or Gram-negative bacteria with FDAAs and/or CDAAs as described herein under conditions where the bacteria can covalently incorporate the FDAAs and/or CDAAs into PG of a bacterial cell wall. The FDAAs and/or CDAAs can be provided to organisms preferably within a given range of concentrations, for example, from about 0.1 µM to about 1 mM, as well as in any whole integer or fractional integer concentration thereof within this preferred range. The FDAAs and/or CDAAs can also be provided to organisms at preferred concentrations, for example, at about 0.1 µM and about 1 mM. Other ranges are also possible besides this preferred range and fall within the scope of this disclosure, the specific identification of which depends upon the particular biological organism or system under study, as well as upon the nature of the FDAAs and/or CDAAs used, their physiochemical properties and uptake by the particular biological organism or system under study, as well as the experimental set-up and purpose of the study at hand, as one of skill in the art would understand.

Determination of the optimal concentration (or amount) of FDAAs and/or CDAAs and the preferred ranges thereof for a particular organism is the subject of routine experimentation well within the purview of those skilled in the art. A typical route to ascertaining the optimal concentrations and preferred ranges of the FDAAs and/or CDAAs described herein is to perform a dose response experiment, wherein the parallel populations of a given organism are contacted with different concentrations (or amounts) of a given FDAA and/or CDAA, and the extent of incorporation of the compound(s) is assessed by biochemical assay (e.g., extent of compound labeling in PG fractions) and/or by visualization methods (e.g., fluorescence microscopy). Other approaches to selecting the optimal concentration (of amount) of FDAAs and/or CDAAs and the preferred ranges thereof for a particular organism are viable as well, as one skilled in the art would readily appreciate based upon this disclosure.

The methods also can include detecting the FDAAs and/or CDAAs in the bacterial cell wall to verify that they have been incorporated. The FDAAs and/or CDAAs (after being clicked) can be detected via fluorescence microscopy and other methods, depending upon the type of label or reporter used.

Screening Methodologies

The cell wall biosynthetic pathway is unique to bacterial cells; therefore, agents that inhibit steps within this pathway are anticipated to show selective toxicity toward bacterial cells. As such, methods of the invention also can include screening for putative cell wall-acting or cell wall-disrupting agents. As used herein, "cell wall-acting" means an ability of an agent to interfere with PG biosynthesis in a bacterial cell wall, especially at the transglycosylation step, as this step takes place on the outer leaflet of the cell membrane so cellular penetration is not a prerequisite for the agent to manifest its biological activity. As used herein, "cell wall-disrupting" means an ability of an agent to disrupt or weaken the integrity of PG in an existing bacterial cell wall.

The methods can begin by contacting bacteria with a putative cell wall-acting agent or putative cell wall-disrupting agent, where the agent is cell wall-acting if the agent interferes with ongoing peptidoglycan biosynthesis in a bacterial cell wall or is cell wall-disrupting if the agent weakens integrity of peptidoglycan in an existing bacterial cell wall. When screening for putative cell wall-acting agents, the bacteria can be co-contacted with FDAAs and/or CDAAs as described herein simultaneously with the putative agent. When screening for putative cell wall-disrupting agents, the bacteria can have FDAAs and/or CDAAs as described herein covalently incorporated into PG of the cell wall prior to being contacted with the putative agent.

The methods also can include detecting whether the FDAAs and/or CDAAs have been incorporated in the bacterial cell wall or whether the FDAAs and/or CDAAs remain in the bacterial cell wall. As noted above, the FDAAs and/or CDAAs (after being clicked) can be detected via fluorescence microscopy and other methods, depending upon the type of label or reporter used. The pattern and/or location of FDAAs and/or CDAAs incorporation can be used to identify the bacteria (see, e.g., FIGS. 10-12).

The methods also can include comparing the results from the putative cell wall-acting agent or cell wall-disrupting agent with a known cell wall-acting agent or known cell wall-disrupting agent.

The compounds of the present disclosure have utility for identifying bacteria. As demonstrated in the Examples set forth herein, certain bacterial species display unique specificity for incorporating certain D-amino acids in PG and the bacteria cell wall. Thus, the use of the disclosed modified D-amino acids of the present disclosure enable identification of bacterial species by virtue of the pattern of labeling observed in the bacteria as a result of incorporation of the modified D-amino acids into PG of the bacterial cell wall.

EXAMPLES

The invention will be more fully understood upon consideration of the following non-limiting examples, which are offered for purposes of illustration, not limitation.

Example 1

Figure 3:
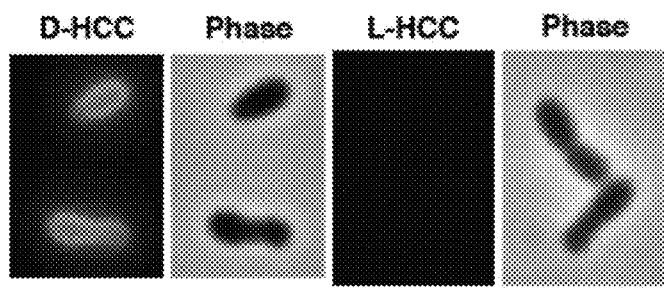
FIG. 3 shows results of control experiments in which the cell walls of *Agrobacterium tumefaciens* ("*A. tumefaciens*" top row), *Bacillus subtilis* ("*B. subtilis*" middle row) and *Escherichia coli* ("*E. coli*" bottom row) were fluorescently labeled with fluorescent D-Ala (D-HCC) or fluorescent L-Ala (L-HCC). An exemplary structure for D-Ala (D-HCC) also is shown in the bottom row.
Figure 3:
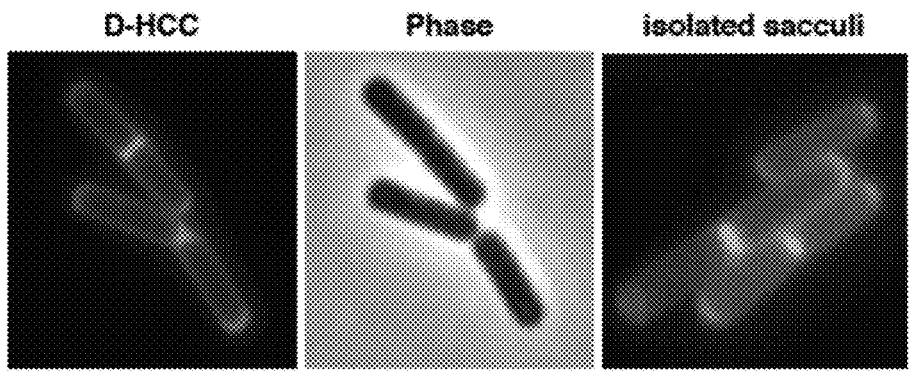
Figure 3:
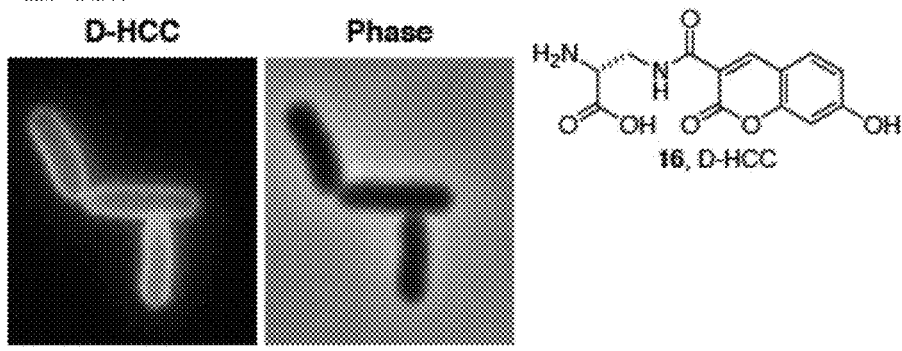

Control experiments were carried out in *A. tumefaciens*, *B. subtilis* and *E. coli* with fluorescent D-Ala (D-HCC) and fluorescent L-Ala (L-HCC). For example, experiments in *A. tumefaciens* revealed that only D-HCC was incorporated into the cell wall. This observation was true for all strains tested. Likewise, experiments with *B. subtilis* revealed predominant labeling at the septum, a result consistent with this being the site of active cell wall synthesis. Subsequent isolation of peptidoglycan from these cells also revealed that isolated sacculi retained the fluorescent label (FIG. 3).

In addition, experiments with a *B. subtilis* dacA mutant (DacA is a D,D-carboxypeptidase that cleaves the terminal D-Ala from the peptide stem) resulted in uniform labeling of the cell wall, which suggested the dominant mode of labeling in *B. subtilis* is at the terminal position of the peptide stem.

Figure 4:
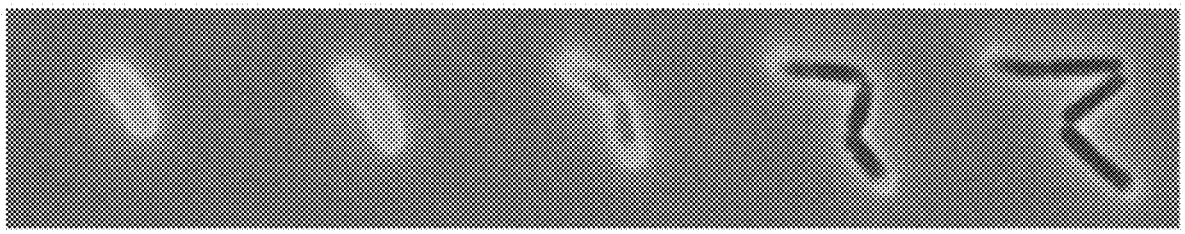
FIG. 4 shows results of a pulse chase experiment with a fluorescent D-Ala in *B. subtilis* (top row) or *A. tumefaciens* (bottom row).
Figure 4:
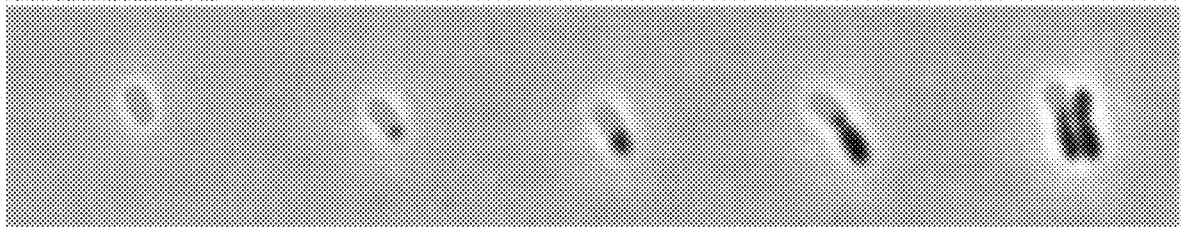

A series of pulse-chase experiments were performed in which exponentially growing cells were diluted and treated with one of the D-Ala probes (250 µM-500 µM), The cells were incubated until saturation, washed, and placed on LB-containing agar pads and imaged at 5-minute intervals for 12-18 hours (FIG. 4).

An experiment in *B. subtilis* revealed that fluorescence persisted at the cell poles, an observation that is consistent with the notion that there is not active cell wall synthesis taking place in these regions (FIG. 4). Interestingly, the labeling pattern observed with *A. tumefaciens* provides supporting evidence for a mode of growth that involves budding as no signal dilution from the mother cell is observed as recently shown.

Figure 5:
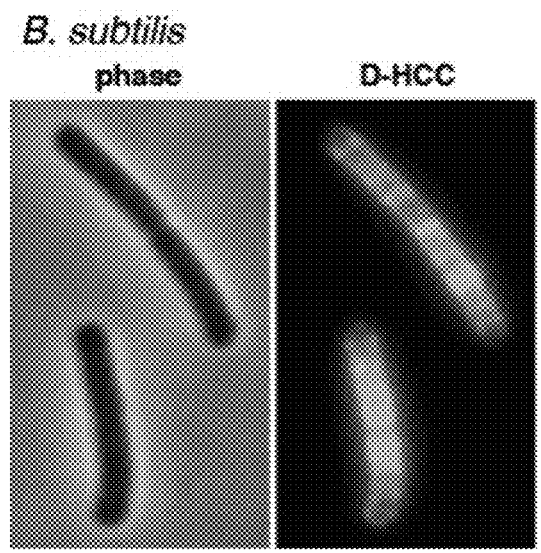
FIG. 5 shows results of a short pulse experiment with fluorescent D-Ala in *B. subtilis*.

More significantly, short exposures to FDAA derivatives have proven to be optimal for imaging the sites of active cell wall biosynthesis. For example, when a culture of exponentially growing cells is contacted with either D-NBD or D-HCC, and the cells were pulsed for 2%-8% of their usual generation time and immediately fixed, sites of active synthesis were clearly visible in evolutionarily distinct bacteria such as *E. coli*, *B. subtilis*, *A. tumefaciens*, *L. lactis*, *M. conglomeratus*, *C. crescentus* and *S. aureus*. Significantly, with experiments conducted in *B. subtilis*, these short pulses result in a staining pattern that appears to be consistent with the helical pattern that has been observed with fluorescently modified vancomycin/ramoplanin (FIG. 5).

Figure 6:
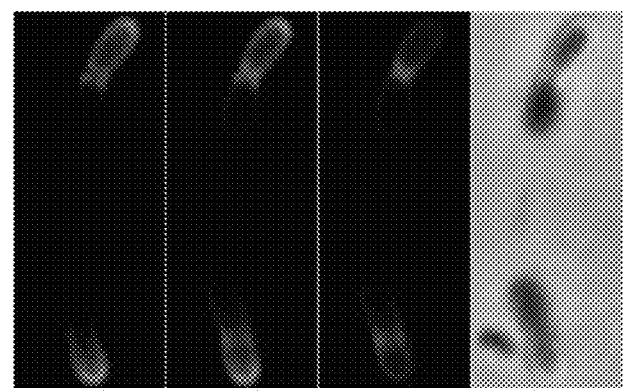
FIG. 6 shows results of a fluorescent D-Ala derivative in a dual-labeling format.

Finally, experiments were performed with the labeled D-Ala derivative in a dual-labeling format. For example, *A. tumefaciens* cells were incubated for a period of 4 minutes in 500 µM D-NBD, followed by washing and incubation for 4 minutes in 500 µM D-HCC. The excess dye was removed and the cells were pelleted and fixed. The fluorescence micrographs reveal distinct patterns of growth, in terms of polar growth and septal synthesis, based on the age of the daughter cell (FIG. 6).

Example 2

Methods

Synthesis of Fluorescent D-Amino Amino Acids (FDAAs)

HADA/HALA: To a flame-dried flask, 7-hydroxycoumarin-3-carboxylic acid (HCC) was added in anhydrous DMF (14.5 mL, 0.1 M) under an atmosphere of argon. Carbonyldiimidazole (236 mg, 1.455 mmol) was added in one portion and stirred at room temperature (RT) for 2 hours. Boc-D-2,3-diaminopropionic acid (for HADA) or Boc-L-2,3-diaminopropionic acid (for HALA) (297 mg, 1.455 mmol) was added in one portion and the reaction mixture was allowed to stir at RT overnight (17 hours). The majority of the solvent was removed in vacuo, and the product was diluted with EtOAc (100 ml) and washed with 1 N HCl (50 ml) and water (100 ml). The water layers were combined and back-extracted with EtOAc (50 ml) to prevent loss of product due to an emulsion. The organic layers were combined, washed with brine (50 ml), dried over $Na_2SO_4$, filtered, and the solvent was removed in vacuo. Without further purification the crude product was treated with trifluoroacetic acid/dichloromethane (50:50, 10 ml) for 30 minutes at RT, and the solvent was removed in vacuo. The product was purified via reverse-phase HPLC with 10%-90% $MeCN/H_2O$. The pure fractions were concentrated in vacuo, and the product was redissolved in 1 N HCl/MeCN and lyophilized to yield the desired product as a pale yellow solid (297 mg, 62% for HADA and 277 mg, 58% for HALA). $[\alpha]^{20}_D = -21.8°$ (c 2.2, DMSO-d6); HRMS-ESI-TOF m/z calc'd for $C_{13}H_{12}O_6N_2$ ($[M+H]^+$): 293.0774, Found 293.0774; HPLC: tR=5.96 min (10-90% $MeCN/H_2O$ over 10 minutes); $^1H$ NMR (400 MHz, DMSO-d6) δ=2.46 (s, 1H), 3.69-3.77 (m, 1H), 3.79-3.87 (m, 1H), 4.07 (t, J=5.6 Hz, 1H), 6.85 (d, J=2.0 Hz, 1H), 6.89 (dd, J=2.0, 8.4 Hz, 1H), 7.89 (d, J=8.8 Hz, 1H), 8.43 (br s, 3H), 8.76 (s, 1H), 8.86 (t, J=6.2 Hz, 1H), 11.34 (br s, 1H); $^{13}C$ NMR (100 MHz, DMSO-d6): δ=52.1, 102.3, 111.3, 113.5, 115.0, 132.5, 148.8, 156.8, 161.2, 163.1, 164.6, 169.7; the signal for one carbon was overlapping with the solvent peak.

NADA/NALA: Boc-D-2,3-diaminopropionic acid (for NADA) or Boc-L-2,3-diaminopropionic acid (for NALA) (100 mg, 0.49 mmol) and sodium bicarbonate (123 mg, 1.47 mmol) were dissolved in water (1.8 ml) and heated to 55° C. in water bath. A solution of 4-chloro-7-nitrobenzofurazan (NBD, 108 mg, 0.539 mmol) in methanol (8.5 ml) was added dropwise over 10 minutes. Care was taken at all times to avoid excessive exposure to light during the reaction and workup. The reaction was allowed to stir at 55° C. for 1 hour. The solvent was removed in vacuo and acidified with 1 N HCl. The aqueous mixture was extracted with dichloromethane (50 ml per extraction×3 extractions) and the organic extracts were washed with brine (50 ml), dried over $Na_2SO_4$, filtered, and the solvent was removed in vacuo. Without further purification the crude product was treated with 4 N HCl/dioxane (10 ml) for 1 hour at RT, and the solvent was removed in vacuo. The product was purified via reverse-phase HPLC with 20%-90% $MeCN/H_2O$. The pure fractions were concentrated in vacuo, and the product was redissolved in 1 N HCl/MeCN and lyophilized to yield the desired product as a bright orange solid (105 mg, 71% for both NADA and NALA). $[\alpha]^{20}_D = -32°$ (c 1.1, DMSO-d6) HRMS-ESI-TOF m/z calc'd for $C_9H_9O_5N_5$ ($[M+H]^+$):

268.0682, Found 268.0680; HPLC: tR=5.02 minutes (20-90% MeCN/H$_2$O over 10 minutes). $^1$H NMR (400 MHz, DMSO-d6): δ=4.06 (m, 2H), 4.29 (m, 1H), 6.61 (d, J=8.0 Hz, 1H), 8.56 (d, J=8.0 Hz, 1H), 8.66 (br s, 3H), 9.32 (br s, 1H); $^{13}$C NMR (100 MHz, DMSO-d6): δ=43.4, 51.5, 100.5, 122.5, 138.1, 144.4, 144.9, 145.2, 169.2.

FDL: To a flame dried flask was added Nα-Boc-D-Lys-OH (19.3 mg, 0.078 mmol) and fluorescein isothiocyanate (25 mg, 0.065 mmol) in dry DMF (0.65 ml). The reaction was stirred under argon at room temperature for 4 hours. The solvent was removed in vacuo. The residue was redissolved in ethyl acetate (10 ml), washed with 1 N HCl (10 ml) and brine (10 ml), and dried over anhydrous sodium sulfate. The solvent was again removed in vacuo, and the crude product was treated with trifluoroacetic acid/dichloromethane (1:1) for 0.5 hours. The acid was removed in vacuo, and the product was purified by reverse phase HPLC with 30%-45% MeCN/H$_2$O. The pure fractions were lyophilized to yield the product as a dark yellow solid (25.0 mg, 72%). $[\alpha]^{20}_D$=−7.1° (c 0.72, MeOH-d4); HMRS-ESI-TOF m/z calc'd for C$_{27}$H$_{26}$N$_3$O$_7$S ([M+H]+): 536.1492, Found 536.1470; HPLC: tR=5.08 min (30%-45% MeCN/H$_2$O over 10 minutes); $^1$H NMR (400 MHz, MeOD-d4): δ=1.50-1.63 (m, 2H), 1.78 (quintet, J=7.0 Hz, 2H), 1.90-1.99 (m, 1H), 2.00-2.10 (m, 1H), 3.66 (br s, 2H), 4.00 (t, J=6.3 Hz, 1H), 6.59 (dd, J=8.8 Hz, 2H), 6.73 (s, 2H), 6.74 (d, J=8.90 Hz, 2H), 7.18 (d, J=8.2 Hz, 1H), 7.76 (d, J=8.2 Hz, 1H), 8.17 (s, 1H); $^{13}$C NMR (100 MHz, MeOD-d4): δ=23.3, 29.5, 31.3, 45.0, 53.9, 103.5, 111.9, 114.1, 120.5, 126.1, 129.2, 130.5, 131.8, 142.5, 154.6, 162.1, 171.0, 171.9, 182.9.

TDL: To a flame dried flask was added Nα-Boc-D-Lys-OH (3.3 mg, 0.0134 mmol), 5-(and 6-) carboxytetramethylrhodamine succinimidyl ester (5 mg, 0.0095 mmol), and diisopropylethylamine (2.5 μl, 0.0143 mmol) in dry DMF (0.2 ml). The reaction was stirred under argon at room temperature overnight. The solvent was removed in vacuo, and the crude mixture was treated with trifluoroacetic acid/dichloromethane (1:1) for 0.5 hours. The reaction was dried in vacuo, and purified by reverse-phase HPLC with 20%-40% MeCN/H$_2$O. The pure fractions were lyophilized to yield the product as a deep red solid (4.6 mg, 61%). $[\alpha]^{20}_D$=−210° (c 0.20, MeOH-d4); HRMS-ESI-TOF m/z calc'd for C$_{13}$H$_{35}$N$_4$O$_6$ ([M+H]$^+$): 599.2557, Found 599.2559; HPLC: tR=7.86 and 9.06 minutes (2 isomers isolated results from mixed isomer starting material) (20%-40% MeCN/H$_2$O over 10 minutes); $^1$H NMR (400 MHz, MeOD-d4): δ=1.25-1.35 (m, 2H), 1.46-1.62 (m, 2H), 1.68 (quintet, J=7.2 Hz, 2H), 1.75-2.05 (m, 2H), 3.41 (t, J=7 Hz, 1H), 3.92 (t, J=Hz, 1H), 7.01 (d, J=2 Hz, 2H), 7.05 (dd, J=2.0 Hz, 9.4 Hz, 2H), 7.13 (d, J=9.4 Hz, 2H), 7.81 (d, J=1.5 Hz, 1H), 8.19 (dd, J=1.5 Hz, 8.6 Hz, 1H), 8.39 (d, J=8.6 Hz, 1H).

Spectral Characteristics of FDAAs

Excitation and emission spectra of FDAAs (500 μM in 100 mM Tris pH 7.0) were determined in black 96-well polystyrene plates (Corning) using top-read function of a Spectra Max M2 plate reader. The excitation and emission spectra were measured in separate runs within a range of 200 nm and with increments of 1 nm.

Click Chemistry

EDA and ELA, and Sulfo-Cy3-Azide were gifts from Boaopharma and Lumiprobe, respectively. AZA and "clickable" Alexa 488 Fluors were purchased from Iris Biotech GmbH and Invitrogen, respectively. The Cu(I) catalyzed click chemistry was performed using the chemicals supplied by Invitrogen following their standard protocol once the cells had been fixed with EtOH (70% v/v) and permeabilized with methanol (100% v/v).

Growth Conditions

Strain characteristics and growth conditions are described in Table 2.

TABLE 2

Strains, their predicted PG chemotypes and conditions for growth and labeling.

| Species | Strain | Source | Gram | PG Chemotype[6] | Media | [HADA] (mM)* | Temperature (° C.) | Aeration |
|---|---|---|---|---|---|---|---|---|
| *Bacillus subtilis* | PY76 | Daniel Kearns IUB | + | A1γb[7] | LB[8] | N/A | 37 | Y |
| *Bacillus subtilis* | PY76, dacA::cam | Daniel Kearns IUB | + | A1γb | LB | 1 | 37 | Y |
| *Bacillus subtilis* | CU1065 | John Helmann CU | + | A1γb | LB | N/A | 37 | Y |
| *Bacillus subtilis* | HB0048-CU1065, dltA::spc | John Helmann CU | + | A1γb | LB | N/A | 37 | Y |
| *Brachybacterium conglomeratum* | | IUB culture collection | + | A4γ | LB | 1 | 30 | Y |
| *Lactococcus lactis* | | IUB culture collection | + | A4α | LB | 1 | 37 | Y |
| *Staphylococcus aureus* | | IUB culture collection | + | A3α | LB | 1 | 37 | N |
| *Streptococcus pneumoniae* | IU1945 | Malcolm Winkler IUB | + | A1α & A3α[5] | BHI[9] | 0.5 | 37 | N |
| *Streptomyces venezuelae* | | Justin Nodwell MU | + | A3γ | LB | 0.5 | 30 | Y |
| *Agrobacterium tumefaciens* | | Yves Brun IUB | − | A1γ | LB | 1 | 26 | Y |
| *Burkholderia phytofirmans* | | Ann Hirsch UCLA | − | A1γ | LB | 0.5 | 30 | Y |
| *Caulobacter crescentus* | YB5630-CB15 ΔrsaΔhfsA | Yves Brun IUB | − | A1γ | PYE[10] | 0.5 | 30 | Y |
| *Escherichia coli* | MG1655 | Patricia Foster IUB | − | A1γ | LB | 1 | 37 | Y |

TABLE 2-continued

Strains, their predicted PG chemotypes and conditions for growth and labeling.

| Species | Strain | Source | Gram | PG Chemotype[6] | Media | [HADA] (mM)* | Temperature (° C.) | Aeration |
|---|---|---|---|---|---|---|---|---|
| Synechocystis sp. PCC 6803 | | David Kehoe IUB | − | A1γ | BG-11[11] | 1 | 26 | $CO_2$ + artificial sunlight |
| Verrucomicrobium spinosum | | Naomi Ward UW | − | A1γ | VM[12] | 0.25 | 30 | Y |

Key:
IUB = Indiana University Bloomington
CU = Cornell University
MU = McMaster University
UCLA = University of California, Los Angeles UW = University of Wyoming
*Short pulse concentrations. By default, a normalized 1% (v/v) DMSO concentration was used for all labeling experiments.

For any experiment involving FDAAs and/or CDAAs, DMSO was added to the growth media to a final concentration of 1% to help solubilize the FDAAs and/or CDAAs. Presence of 1% DMSO did not affect labeling or growth in bacteria tested. When necessary, chloramphenicol or spectinomycin was added to the growth media at 5 μg/ml or 100 μg/ml, respectively. Strains were maintained on plates containing growth media with 1.5% agar.

Growth Curves

For growth curves, exponentially growing E. coli, A. tumefaciens and A. tumefaciens and B. subtilis ΔdacA were diluted to $OD_{600}$ 0.05 into wells of polystyrene 24-well plates (Falcon) containing 750 μl LB with 1% DMSO or 1% DMSO+FDAAs (250 μM-1 mM). The absorbance at 600 nm was read every 5 minutes for 18 hours in a BIO-TEK Synergy HT Plate Reader (30° C., static).

Short Labeling Pulses and Fluorescence Microscopy

Figure 11:
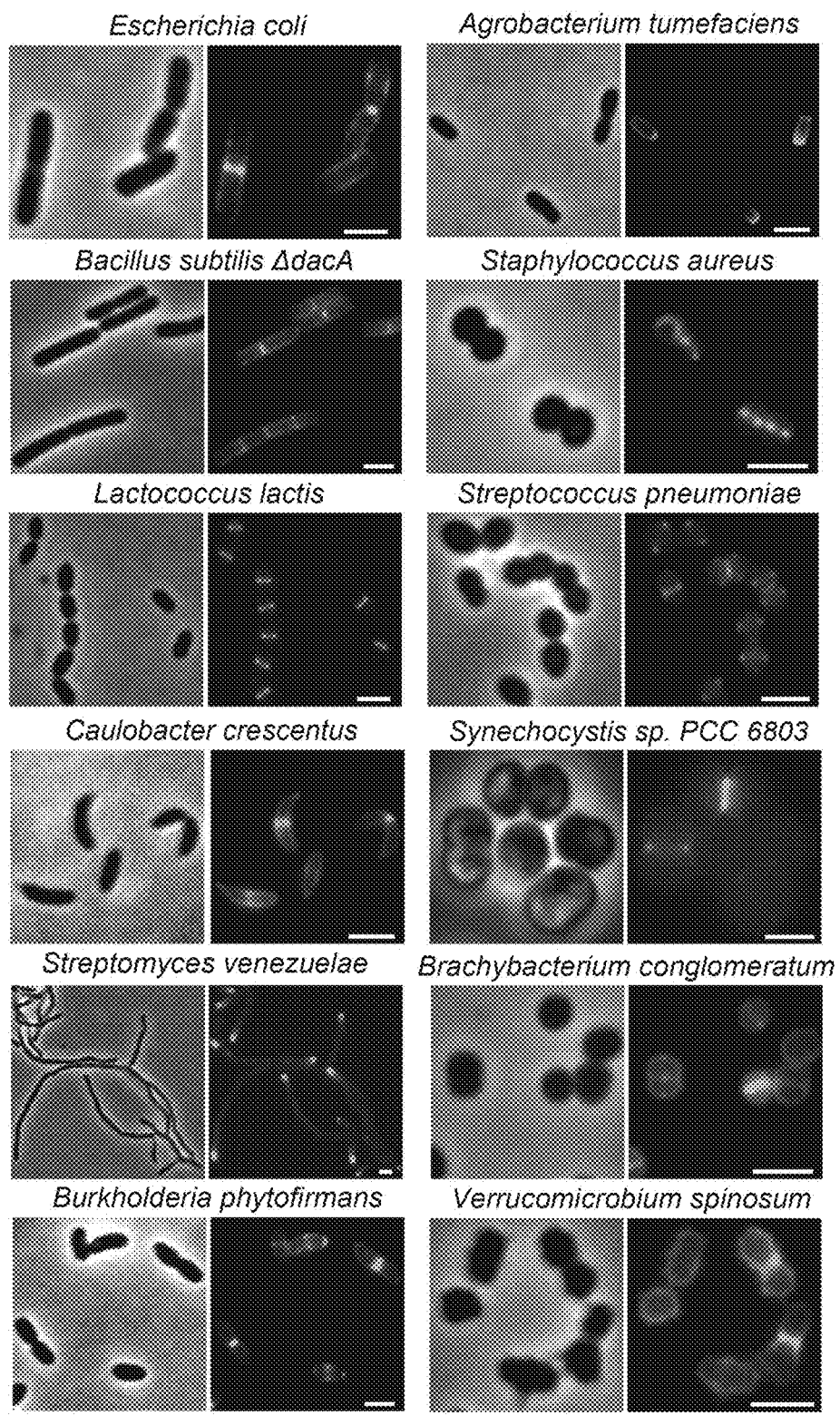
FIG. 11 shows that short pulses of HADA label distinct modes of growth in diverse bacteria. Strains were labeled for ~2%-8% of the doubling time: *E. coli* (30 seconds), *A. tumefaciens* (2 minutes), *B. subtilis* ΔdacA (30 seconds), *S. aureus* (2 minutes), *L. lactis* (2 minutes), *S. pneumoniae* (4 minutes), *C. crescentus* (5 minutes), *Synechocystis* sp. PCC 6803 (1 hour), *S. venezuelae* (2 minutes), *B. conglomeratum* (8 minutes), *B. phytofirmans* (20 minutes), *V. Spinosum* (10 minutes). Scale bars, 2 μm.
Figure 12:
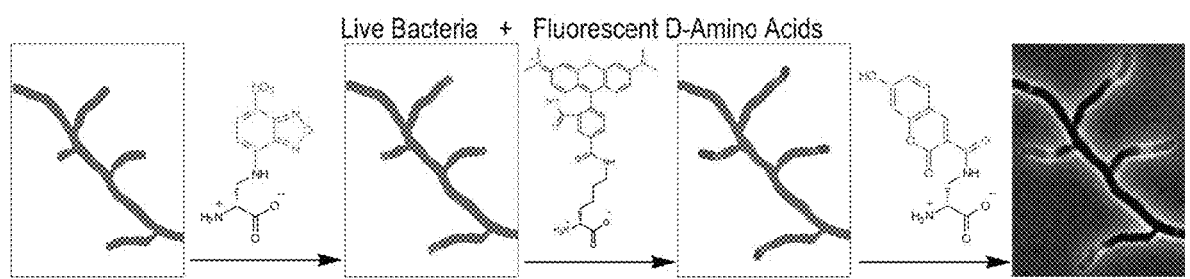
FIG. 12 shows a schematic for sequentially incorporating distinct FDAAs, such as NADA, TDL and HADA, into newly synthesized PG in live bacteria.

For short labeling pulses, exponentially growing cells were screened for the minimum concentration of FDAAs or CDAAs (250 μM-1 mM) and minimum amount of exposure duration to identify the optimal conditions for each bacterium, as shown in FIG. 11 and Table 2. To image growth patterns in different species, exponentially growing cells ($OD_{600}$~0.3) were labeled, fixed, washed, "clicked" if appropriate, and imaged.

For most strains, excess dye was removed by washing the cells three to four times with 1 ml 1×PBS (NaCl 8 g/L, KCl 0.2 g/L, $Na_2HPO_4$-$2H_2O$ 1.78 g/L, $KH_2PO_4$ 0.27 g/L, pH 7.4) and pelleting for 2-5 minutes at 10,000-16,000×g in a microfuge. When required, cells were fixed with EtOH (70%, ice-cold, 20-minute incubation). Exceptions included S. pneumoniae (1% gluteraldehyde, 20 minutes incubation) and B. subtilis (cold PBS treatment).

For dual labeling, the same procedure was followed with the addition of a second round of a short labeling pulse using the second FDAA prior to fixation. Cells were washed before, between and after each FDAA treatment with prewarmed medium in order ensure similar labeling conditions. For triple labeling, a third round of labeling involving CDAAs was added. For dual and triple labeling of A. tumefaciens, the incubation times with each label were 5 minutes and 7 minutes, respectively.

Phase and fluorescence microscopy was performed with a Nikon® 90i Fluorescence Microscope equipped with a Plan Apo 100×/1.40 Oil Ph3 DM Objective and a Chroma 83700 triple filter cube with corresponding excitation and emission filters (DAPI for HADA/HALA; FITC for NADA/NALA; and Alexa Fluor® 488s and Texas Red® for Sulfo-Cy3 or WGA-594). All images were captured using NIS software from Nikon® and a Photometrics Cascade 1K cooled charge-coupled device camera, and were processed and analyzed using ImageJ. When a comparison was made, cultures were treated in exactly the same manner and the same parameters were applied for collecting and post processing of the microscopy data.

Long Labeling Pulses and Time-Lapse Microscopy

Exponentially growing cells were diluted to $OD_{600}$ 0.05 in media containing half of the optimal FDAA concentration used for short labeling pulses and were grown until late exponential phase. The cells were fixed, washed and then imaged using the Nikon® 90i as described previously. For time-lapse microscopy the cells were washed with media and mounted onto LB+1% (w/v) agarose pads on 25-mm by 75-mm glass slides, sealed with 1:1:1 mixture of vasoline, lanolin and paraffin and imaged with intervals of 4 minutes (B. subtilis ΔdacA), 5 minutes (E. coli) or 10 minutes (A. tumefaciens) using a Nikon® Ti-E Inverted Fluorescence Microscope equipped with a Plan Apo 60×/1.40 Oil Ph3 DM Objective and a CFP/YFP filter cube and an Andor DU885 EMCCD Camera using CFP settings for detection of HADA.

Super-resolution Microscopy

Structured illumination microscopy was performed using a DeltaVision® OMX Imaging System equipped with an Olympus® UPlanSApo 100×/1.40 Oil PSF Objective and a Photometrics Cascade II EMCCD Camera. The samples were excited with a laser at 405 nm and the emission was detected through a 419-465 emission filter.

Environmental Samples

HADA (500 μM+1% DMSO) and/or NADA (500 μM+1% DMSO) was added to either a 1.5 ml saliva sample from a 26-year old male or to a 1.5 ml concentrated (~10 times) fresh water sample collected from Indiana University and incubated for 2 hours (HADA) at 37° C. or for 2 hours (HADA) and 2 hours (NADA) at 26° C., respectively. The samples were then fixed, washed and imaged.

Live-Dead Staining

E. coli cells were labeled with HADA in 0.1% DMSO. Cells were subsequently stained using the LIVE-DEAD BacLight Kit (Invitrogen) according to the manufacturer's standard protocol.

Sacculi Purification

Sacculi from cells were purified as described in Litzinger et al. (2010) J. Bacteriol. 192:3122-3143 with following modifications. Exponentially growing cells were diluted to $OD_{600}$ 0.05 in 10 ml LB containing half of the optimum FDAA concentration+1% (v/v) DMSO and grown to late exponential phase. After aliquots were taken for whole cell imaging, cells were collected by centrifugation at 25,000×g for 15 minutes at RT and resuspended in 0.8 ml water. The suspension was added to boiling sodium dodecyl sulfate (SDS, 5% w/v) drop-wise and incubated with stirring for 30 minutes. SDS insoluble material was collected by ultracentrifugation at 39,000×g for 10 minutes at 30° C. and was resuspended in 1 ml water and boiled again in SDS (4% w/v) with stirring for 30 minutes. Samples were then washed four times in 1.5 ml water and resuspended in 1 ml 10 mM Tris-HCl pH 7.0+10 mM NaCl+0.32 M immidazole+α-amylase (100 μm/ml)+DNase I (50 μg/ml)+MgSO$_4$ (1 mM) and incubated for 2 hours at 37° C. Samples were pelleted and resuspended in 0.05 M Tris-HCl pH 7.8+1.4 mg/ml pronase (type XXV from Streptomyces griseus) and incubated 2 hours at 60° C. Samples were again pelleted and resuspended in 1 ml water and boiled in SDS (1% w/v) with stirring for 30 min. The sacculus preparations were washed a final time and resuspended in a minimal amount of water. When needed, sacculi were further stained with Wheat Germ Agglutinin, Alexa Fluor® 594 Conjugate (WGA-594, 15 μg/ml).

HPLC Analysis of PG and Muropeptide Identification

PG from FDAA labeled cells was purified by the boiling SDS extraction method and muramidase digestion treatment (Cellosyl) as previously described in Brown et al. (2012) Proc. Natl. Acad. Sci. USA 109:1697-1701. Solubilized muropeptide mixtures were then either directly injected into the HPLC system (native or non-reduced samples) or subjected to BH$_4$Na reduction as described in Brown et al. (2012), supra. Muropeptides were analyzed using a binary-pump Waters® HPLC System (Waters Corporation) fitted with a reverse phase RP18 Aeris® Peptide Column (250 mm×4.6 mm; 3.6 μm particle size) (Phenomenex) and a dual wavelength absorbance detector. Elution conditions were: flow rate 1 ml/min; temperature 35° C.; 3 minutes isocratic elution in 50 mM sodium phosphate, pH 4.35 followed by a 57 minute linear gradient to 75 mM, sodium phosphate, pH 4.95 in 15% (v/v) methanol (90 mM sodium phosphate, pH 5.2 in 30% (v/v) methanol for B. subtilis analyses), and 10 minute isocratic elution under the gradient final conditions. Elution was monitored setting one channel to 204 nm and the second to a wavelength appropriate for detection of corresponding FDAA. Muropeptides of interest were collected following HPLC separation; vacuum dried, and subjected to MALDI-mass spectrometry and electrospray ionization MS/MS as described in Brown et al. (2012), supra.

Results

Figure 8:
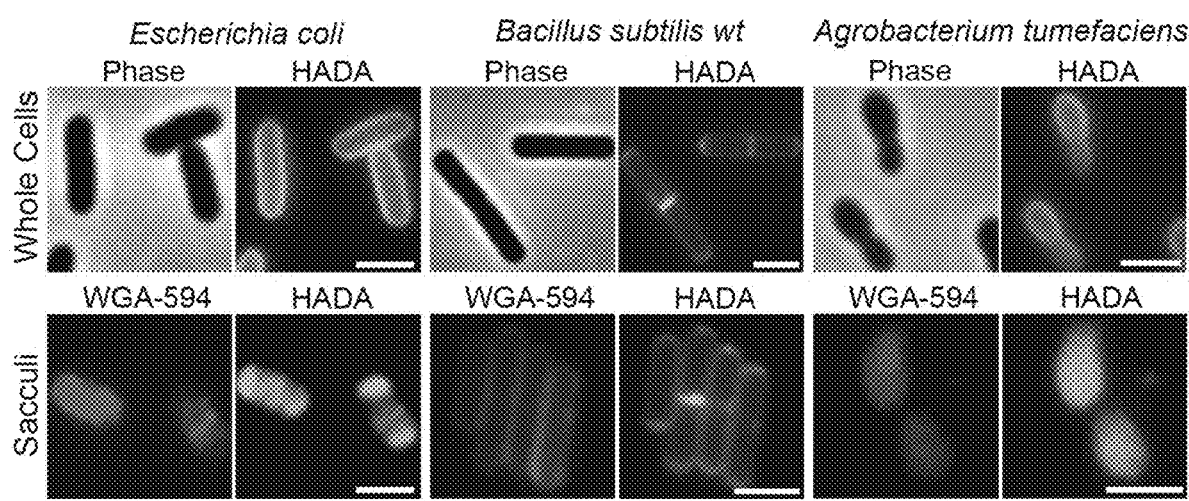
FIG. 8 shows that long labeling pulses with HADA uniformly label PG in live *Escherichia coli* (left), *Bacillus subtilis* (center) and *Agrobacterium tumefaciens* (left). The FDAA fluorescence was retained in isolated sacculi, which also stained with a NAG-specific wheat germ agglutinin (WAG) lectin conjugated to Alexa Fluor® 594 (red). Scale bars, 2 μm.

Growth of the phylogenetically diverse model species E. coli, A. tumefaciens and B. subtilis in the presence of FDAAs for as little as one generation resulted in strong peripheral and septal labeling of entire cell populations (FIG. 8) without affecting growth rate. Neither of the FLAAs prepared from 3-amino-L-alanine resulted in significant labeling, indicating that labeling is specific to the D-enantiomers. The labeling was exclusive to viable cells treated with the FDAAs and was not the result of non-specific interaction of FDAAs with the PG. Additionally, incorporation did not occur into teichoic acids for B. subtilis as indicated by identical labeling of wild-type and a ΔdltA mutant that does not D-alanylate its teichoic acids.

Figure 9B:
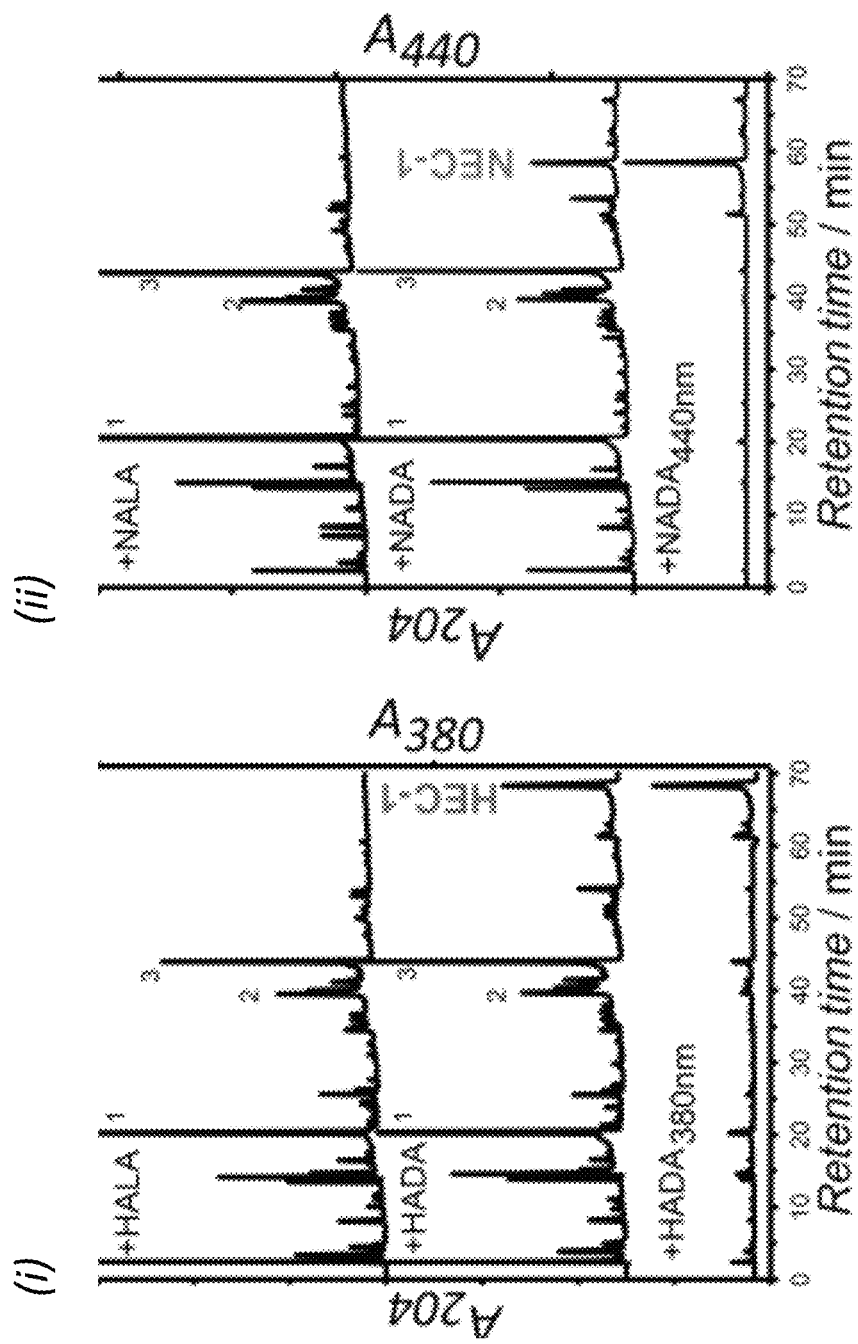
Figure 9D:
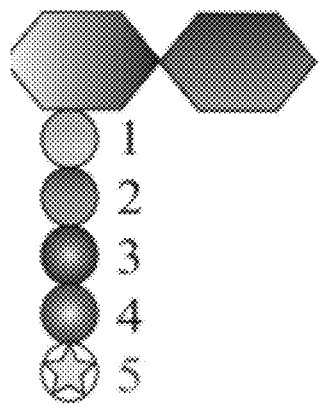
Figure 9D:
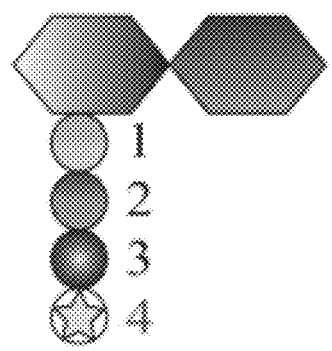

Retained fluorescence on the purified sacculi (FIG. 8) demonstrated that the labeling of PG by the FDAAs was covalent. HPLC analyses of muropeptides isolated from labeled cells (FIGS. 9B-C) revealed that 0.2%-2.8% of total muropeptides were modified (FIG. 9C), which is sufficient for detection in various experiments while avoiding possible toxicity issues that could result from abundant incorporation. Significantly, the FDAA-specific peaks, which were absent in samples treated with FLAAs, could be distinguished from unlabeled muropeptides at FDAA-specific absorption wavelengths (FIG. 9B). MS/MS analyses of FDAA-modified muropeptides in B. subtilis indicated that FDAAs were exclusively incorporated in the fifth position of the stem peptide (FIG. 9D). Interestingly, in a ΔdacA mutant of B. subtilis, the fraction of labeled muropeptides and the fluorescent signal were substantially higher than in wild-type B. subtilis, which is likely due to the D,D-carboxypeptidase activity of DacA. In contrast, the detectable incorporation was solely at the fourth position in E. coli and A. tumefaciens (FIG. 9D). These results are in agreement with the known sites of incorporation of various natural DAAs in these species and suggest that, similar to DAAs, FDAAs incorporate mainly through periplasmic exchange reactions with the muropeptides catalyzed either by D,D-transpeptidases (e.g., in B. subtilis) or by L,D-transpeptidases (e.g., in E. coli and A. tumefaciens). This DAA-like behavior together with the ease of fluorescent detection make FDAAs a novel alternative to radioactive probes for studying in vitro and in vivo activities of PG synthesis enzymes.

Pulse-chase experiments with HADA allowed the real-time tracking of new PG incorporation during growth via time-lapse microscopy. In E. coli and B. subtilis ΔdacA (FIG. 10A), the polar caps retained the HADA signal, but the signal from the lateral walls dispersed as the cells grew, in agreement with previous reports of cell wall growth along the length of the lateral walls.

Figure 10A:
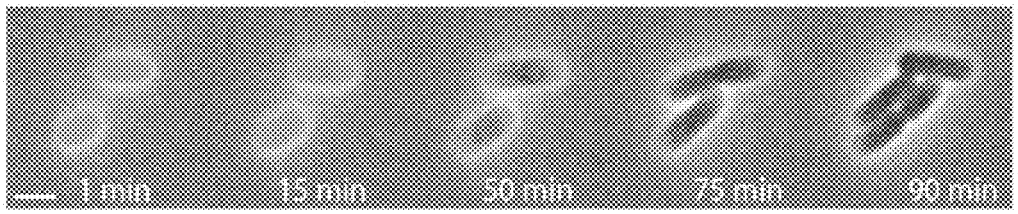
FIGS. 10A-F show FDAAs label diverse bacterial growth patterns. Arrows in the triple labeling panels indicate the sequence of labeling. White scale bars, 2 μm, red scale bars, 1 μm.
Figure 10A:
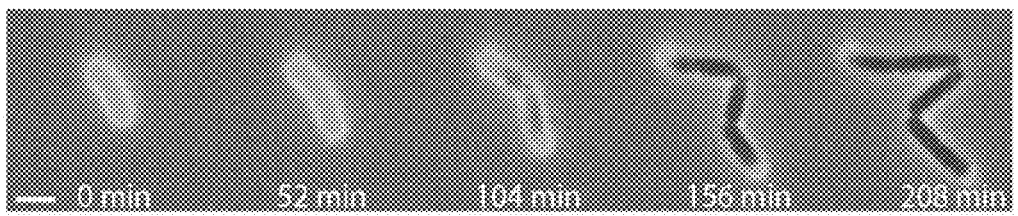
Figure 10B:
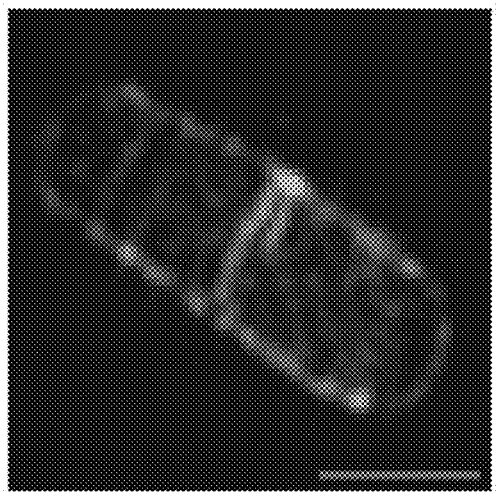
Figure 10B:
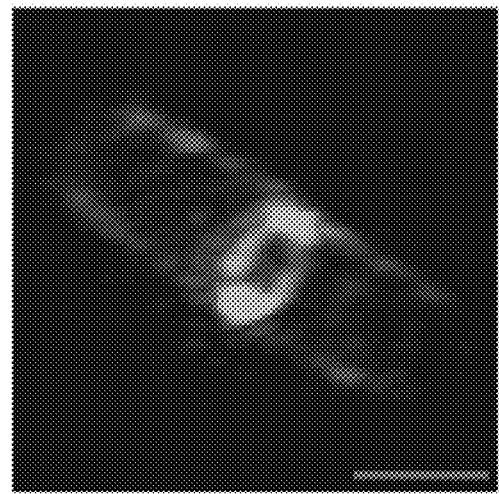
Figure 10C:
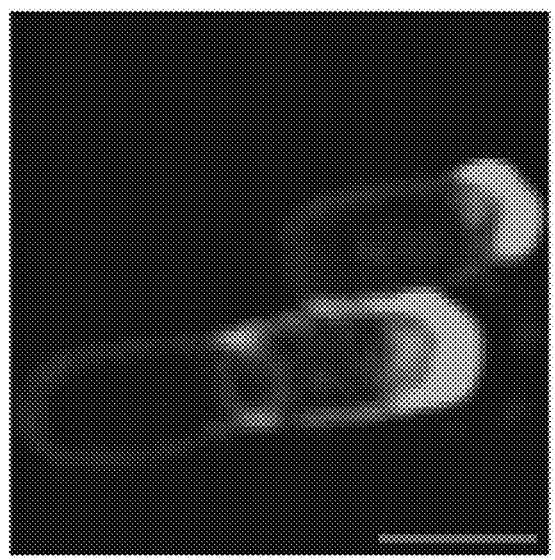

Strikingly, short labeling times (2%-8% of doubling time) using E. coli and B. subtilis ΔdacA with HADA resulted in preferential localization of the signal at the septal plane of predivisional cells and in punctuate patterns on the lateral walls of elongating cells (FIG. 11). Super-resolution microscopy of E. coli revealed reticulated hoop-like patterns of HADA labeling around the lateral wall (FIG. 10B), supportive of bursts of PG incorporation in the side-walls. This ability of FDAAs to resolve insertion of new PG provides the first direct detection of zones of PG synthesis in a structured rather than a random pattern in E. coli, consistent with recent results following the movement of the cell wall elongation machinery. Short labeling times with A. tumefaciens, whose growth occurs predominantly from a single pole and the site of cell division while the mother cell remains inert, resulted in polar and septal labeling. Super-resolution fluorescence microscopy of labeled cells further enhanced the spatial resolution of the site of active PG synthesis (FIG. 10C).

Figure 10D:
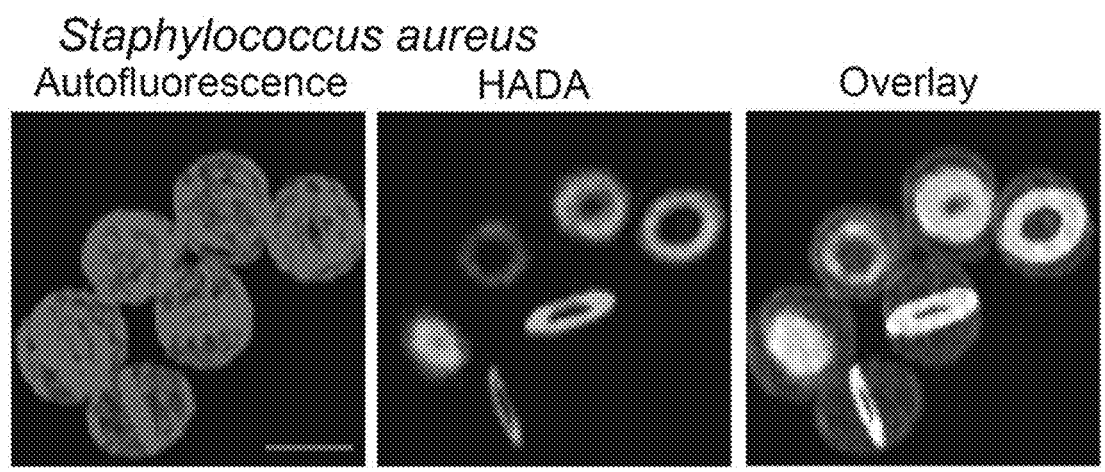
Figure 10E:
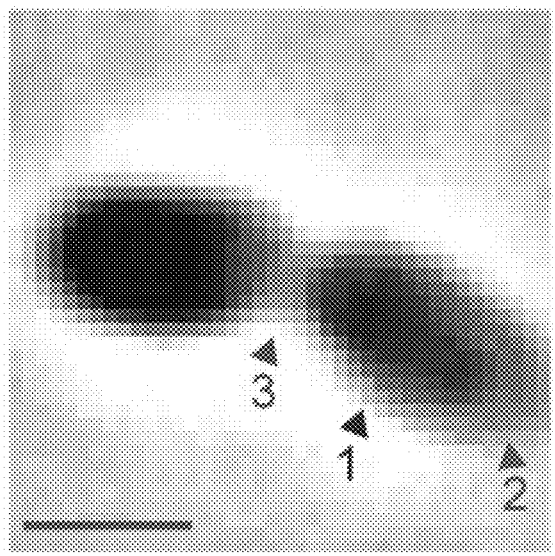

PG labeling in three evolutionarily distant species suggested that FDAAs could specifically label the active site of PG synthesis across the entire bacterial domain. When species representing diverse phyla and modes of growth were briefly incubated with FDAAs, we observed strong labeling at the sites of cell division in actively dividing cells (FIG. 11). This septal probe incorporation was the sole mode in Synechocystis sp. PCC 6803, L. lactis and S. aureus. Super-resolution microscopy of S. aureus further highlighted the different stages of these constricting septal rings (FIG. 10D). Labeling of S. pneumoniae occurred in single or split equatorial rings depending on the length of the cell, with peripheral labeling between the split rings (FIG. 11). Labeling of S. venezuelae was predominantly apical, with some weak labeling of vegetative septa and lateral walls suggestive of a low but continuous lateral PG synthesis (FIG. 11). In C. crescentus, labeling occurred at the sites of septal elongation, lateral elongation, and stalk synthesis (FIG. 11). B. phytofirmans exhibited polar and mid-cell PG synthesis, B. conglomeratum exhibited prominent peripheral PG synthesis in addition to seemingly alternating perpendicular division planes, and *V. spinosum* exhibited strong peripheral PG synthesis and asymmetric septal labeling (FIG. 11).

The efficient label incorporation in all the bacteria indicates that FDAAs, therefore DAAs, incorporation is common to the bacterial domain and that FDAAs can thus be used to analyze natural bacterial populations, providing a convenient and quick standard to measure bacterial activity and to probe the diversity of growth modes in complex microbiomes. Indeed, labeling times with FDAAs as short as 2 hours revealed diverse modes of growth in saliva and freshwater samples in situ, but did not label dead cells as suggested by the strong correlation with Live-Dead staining.

Encouraged by the efficiency of FDAAs, additional and differently functionalized unnatural DAAs were prepared and used. Following a similar approach, a brighter and more versatile core fluorophore, fluorescein (emission maximum ~515 nm, green), and its analogue, carboxytetramethylrhodamine (TAMRA, emission maximum ~565 nm, red) were derivatized and linked with D-Lys to separate the bulky fluorophore from the DAA backbone, generating FDL and TDL (see, for example, structures in FIG. 7). Incubation of both *E. coli* and *B. subtilis* with FDL showed patterns similar to NADA, although labeling of *B. subtilis* was stronger than *E. coli*. In contrast, the larger TDL did not label *E. coli* cells, but labeling of *B. subtilis* was prominent and showed patterns similar to other FDAAs.

CDAAs, namely ethynyl-D-alanine (EDA) or azido-D-alanine (ADA) (FIG. 7), that can be specifically captured by any molecule carrying the conjugate functional group via click-chemistry also were used. Similar to FDAAs, these bioorthogonal DAAs, but not the L-enantiomer control ELA, labeled both *E. coli* and *B. subtilis* when captured by commercially available azido/alkyne fluorophores.

Figure 10F:
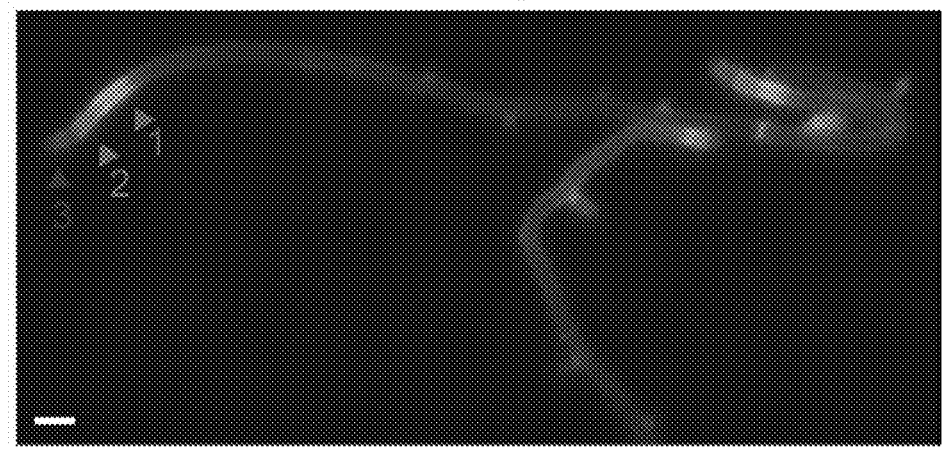

Furthermore, custom DAAs containing different colored fluorophores can be used sequentially to enable "virtual time-lapse microscopy." Since addition of each new probe indicates the location and extent of PG synthetic activity during the respective labeling periods, this approach provides a chronological account of shifts in PG synthesis of individual cells over time. Examples of such serial labeling, including a combination with click chemistry, were performed in Gram-negative *A. tumefaciens* (FIG. 10E) and in Gram-positive *S. venezuelae* (FIG. 10F).

In view of the foregoing, disclosed herein are compositions for and methods of covalently labeling PG in live bacterial cells. This method works very efficiently in both Gram-positive and Gram-negative organisms (Gram-negative organisms represent a liability for approaches using fluorescently modified vancomycin/ramoplanin), and the probe substrates do not appear to be toxic to cells and show no adverse effects on cell morphology, even at concentrations as high as 1 mM. The probes rapidly label sites of active peptidoglycan biosynthesis and can be used in time-lapse and dual labeling experiments.

Thus, compositions and methods have been described herein for in situ labeling/probing of PG synthesis in bacteria with fluorescent D-amino acids (FDAAs), as well as for screening for bacterial cell wall-acting and/or cell wall-disrupting agents. The FDAAs are based upon D-amino acids (DAAs) derivatized to covalently include a small fluorophore. As such, the FDAAs can be directly incorporated into bacterial cell walls during PG biosynthesis, as occurs at sites of cell division in actively dividing cells.

The compositions include FDAAs. The FDAAs have a DAA covalently attached to a fluorophore such as 7-hydroxycoumarin 3-carboxylic acid (HCC—OH), 7-nitrobenzofurazan (NBD), 4-chloro-7-nitrobenzofurazan (NBD-Cl), fluorescein (F) or carboxytetramethylrhodamine (T). The DAA can be any of the twenty known, standard amino acids, such as D-Ala, D-Asp, D-Cys, D-Glu or D-Lys.

The compositions also include clickable DAAs (CDAAs). The CDAAs have a DAA backbone including an alkyne or azide functional group that can be captured by any labeled detecting agent carrying a conjugate functional group via click-chemistry, where the label can be a fluorescent molecule.

The compositions also include fluorescent muramylpentapeptide precursor units (FMPUs). The FMPUs have an N-acetyl muramic acid (NAM) moiety with a stem peptide of three to five amino acids in which one or more of the amino acids in the stem peptides are FDAAs and/or CDAAs as described herein.

The compositions also include fluorescent PG units (FPGUs). The FPGUs have a FMPU as described herein linked to an N-acetyl glucosamine (NAG) moiety.

The compositions also include live bacteria having one or more FDAA, CDAA, FMPU and/or FPGU as described herein incorporated into PG in a cell wall.

The compositions also include kits having one or more FDAA, CDAA, FMPU and/or FPGU as described herein and optionally one or more labeled, detecting agents for use in in situ labeling/probing of PG synthesis, as well as for screening for bacterial cell wall-acting and/or cell wall-disrupting agents. The kits also can include additional reagents such as unlabeled DAAs, unlabeled L-amino acids (LAAs), fluorescent LAAs (FLAAs) and/or clickable LAAs (CLAAs). The kits also can include positive and/or negative bacterial controls, where the bacterial controls have unlabeled DAAs, CDAAs, LAAs and CLAAs and/or labeled DAAs, CDAAs, LAAs and CLAAs incorporated into PG in a cell wall.

In view of the foregoing, the methods have been disclosed herein that include assessing bacterial cell wall synthesis in real time by providing live bacteria with one or more FDAA, CDAA, FMPU and/or FPGU as described herein, where the bacteria covalently incorporate the one or more FDAA, CDAA, FMPU and/or FPGU into PG of a bacterial cell wall. The one or more FDAA, CDAA, FMPU and/or FPGU can be provided to live bacteria together or sequentially during cell wall synthesis.

The methods also include screening for putative cell wall-acting or cell wall-disrupting agents by contacting bacteria with a putative cell wall-acting agent or putative cell wall-disrupting agent, where the agent is cell wall-acting if the agent interferes with ongoing PG biosynthesis in a bacterial cell wall or is cell wall-disrupting if the agent weakens integrity of PG in an existing bacterial cell wall. When screening for putative cell wall-acting agents, the bacteria can be provided with one or more FDAA, CDAA, FMPU and/or FPGU as described herein simultaneously with the putative agent. When screening for putative cell wall-disrupting agents, the bacteria can have one or more FDAA, CDAA, FMPU and/or FPGU as described herein covalently incorporated into PG of the cell wall prior to being contacted with the putative agent.

The methods also include identifying a bacteria by providing live, unknown bacteria with one or more FDAA, CDAA, FMPU and/or FPGU as described herein under conditions sufficient for bacterial cell wall synthesis, where the bacteria covalently incorporate one or more FDAA, CDAA, FMPU and/or FPGU into a cell wall, and where each of the one or more FDAA, CDAA, FMPU and/or FPGU includes a distinct fluorophore. The methods also include observing an incorporation pattern of the one or more FDAA, CDAA, FMPU and/or FPGU, where the incorporation pattern identifies the bacteria. Such methods are amenable for use in screening platforms to identify novel compounds having bacteriostatic or bacteriotoxic properties.

In the methods, the bacteria can be Gram-positive or Gram-negative bacteria.

The methods also include detecting one or more FDAA, CDAA, FMPU and/or FPGU as described herein that have been incorporated in the bacterial cell wall or that have been disrupted from the bacterial cell wall by, for example, fluorescence microscopy and other methods, depending upon the label used.

The methods also can include comparing the results of the putative agent with a known cell wall-acting agent or with a known cell wall-disrupting agent.

The compositions and methods described herein therefore find use in the study of bacterial cell wall biosynthesis and in the discovery of bacterial cell wall-acting and/or cell wall-disrupting agents. Advantageously, the FDAAs, CDAAs, FMPUs and/or FPGUs as described herein simultaneously are non-toxic and can be tunable to label sites of active PG biosynthesis, enabling fine spatiotemporal tracking of cell wall dynamics in phylogenetically and morphologically diverse bacteria.

All of the patents, patent applications, patent application publications and other publications recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

REFERENCES

Typas et al. (2012) Nat. Rev. Microbiol. 10:123-36.
van Dam et al. (2009) Chembiochem 10:617-24.
Daniel & Errington (2003) Cell 113:767-76.
Tiyanont et al. (2006) Proc Natl Acad Sci USA 103: 11033-38.
Olrichs et al. (2011) Chembiochem 12:1124-33.
Sadamoto et al. (2004) J. Am. Chem. Soc. 126:3755-61.
de Pedro et al. (1997) J. Bacteriol. 179:2823-34.
Lam et al. (2009) Science 325:1552-55.
Cava et al. (2011) EMBO J. 30:3442-53.
Lupoli et al. (2011) J. Am. Chem. Soc. 133:10748-51.
Brown et al. (2012) Proc. Natl. Acad. Sci. USA 109:1697-1701.
Mobley et al. (1984) J. Bacteriol. 158:169-79.
Furchtgott et al. (2011) Mol. Microbiol. 81:340-353.
Domínguez-Escobar et al. (2011) Science 333:225-28.
Garner et al. (2011) Science 333:222-225.
Rippka & Herdman (1985) Ann. Inst. Pasteur/Microbiol. 136:33-39.
Zapun et al. (2008) FEMS Microbiol. Rev. 32:345-360.
Flärdh (2003) Curr. Opin. Microbiol. 6:564-571.
Aaron et al. (2007) Mol. Microbiol. 64:938-952.
Young (2006) Microbiol. Mol. Biol. Rev. 70:660-703.
Lavis & Raines (2008) ACS Chem. Biol. 3:142-155.
Decad & Nikaido (1976) J. Bacteriol. 128:325-336.
Prescher & Bertozzi (2005) Nat. Chem. Biol. 1:13-21.
Neumann et al. (2010) Nature 464:441-44.
Wang et al. (2001) Science 292:498-500.
Schneider et al. (2012) Nat. Meth. 9:671-675.
Litzinger et al. (2010) J. Bacteriol. 192:3132-3143.
Brown et al. (2012) Proc. Natl. Acad. Sci. USA 109:1697-1701.
Cava et al. (2011) Embo. J. 30:3442-3453.
Lupoli et al. (2011) J. Am. Chem. Soc. 133:10748-10751.
Schleifer & Kandler (1972) Bacteriological Reviews 36:407-477.
Atrih et al. (1999) J. Bacteriol. 181:3956-3966.
Filipe et al. (2011) J. Biol. Chem. 276:39618-39628.
Sham et al. (2011) Proc. Natl. Acad. Sci. USA 108:E1061-1069.
Shapiro & Agabian-Keshishian (1970) Proc. Natl. Acad. Sci. USA 67:200-203.
Stanier et al. (1971) Bacteriol. Rev. 35:171-205.
Staley & Mandel (1973) Intl. J. System. Bacteriol. 23:271-273.

The invention claimed is:

1. A method of assessing bacterial cell wall synthesis in real time, the method comprising:
providing live bacteria with a first amount of at least one modified amino acid comprising a D-amino acid covalently attached to a fluorescent label selected from the group consisting of $C_{y3B}$ADA, $AF_{647}$ADA, $AF_{350}$ADA, BADA, FADA, HADA, NADA, TADA, YADA, FDL, HDL, NDL, and TDL, and optionally a second amount of at least one additional modified amino acid comprising a clickable D-amino acid, under conditions sufficient for bacterial cell wall synthesis,
wherein the bacteria covalently incorporate the at least one modified amino acid and optionally the at least one additional modified amino acid into a stem peptide of peptidoglycan of the bacterial cell wall.

2. The method of claim 1, wherein the first amount and second amount comprise a first concentration and a second concentration, respectively, wherein the first and second concentrations range from about and including 0.10 μM to about and including 1 mM.

3. The method of claim 1, further comprising detecting a fluorescent signal emitted by the at least one modified amino acid comprising a D-amino acid covalently attached to a fluorescent label, and optionally the at least one additional modified amino acid comprising a clickable D-amino acid incorporated into the stem peptide.

4. The method of claim 1, wherein the bacteria are Gram-positive bacteria or Gram-negative bacteria.

5. The method of claim 1, wherein the at least one additional modified amino acid comprising a clickable D-amino acid is selected from the group consisting of EDA and ETDA.

6. The method of claim 1, wherein the D-amino acid is selected from the group consisting of 3-amino-D-Ala, D-Ala, D-Asp, D-Cys, D-Glu and D-Lys.

* * * * *